US011213318B2

(12) United States Patent
Ginn et al.

(10) Patent No.: US 11,213,318 B2
(45) Date of Patent: Jan. 4, 2022

(54) EXPANDABLE INTRODUCER SHEATH AND METHOD

(71) Applicant: Medtronic, Inc., Minneapolis, MN (US)

(72) Inventors: Richard S. Ginn, Gilroy, CA (US); Michael T. Carley, San Jose, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 615 days.

(21) Appl. No.: 14/934,767

(22) Filed: Nov. 6, 2015

(65) Prior Publication Data
US 2016/0128723 A1    May 12, 2016
US 2019/0183525 A9    Jun. 20, 2019

Related U.S. Application Data

(63) Continuation-in-part of application No. 14/276,952, filed on May 13, 2014, and a continuation-in-part of
(Continued)

(51) Int. Cl.
*A61B 17/34*    (2006.01)
*A61F 2/962*    (2013.01)
(Continued)

(52) U.S. Cl.
CPC ...... *A61B 17/3439* (2013.01); *A61B 17/3468* (2013.01); *A61B 17/3498* (2013.01);
(Continued)

(58) Field of Classification Search
CPC . A61M 25/0021–0023; A61M 25/0662–0668; A61M 2025/0024–0025;
(Continued)

(56) References Cited

U.S. PATENT DOCUMENTS 4,655,771 A    4/1987 Wallsten
4,723,549 A    2/1988 Wholey et al.
(Continued)

FOREIGN PATENT DOCUMENTS

AU    2012335016 A1    5/2014
AU    2012335016 B2    7/2017
(Continued)

OTHER PUBLICATIONS

International Search Report and Written Opinion dated Oct. 17, 2014, International Patent Application No. PCT/US14/037924 with International Filing Date of May 13, 2014 (13 Pages).
(Continued)

*Primary Examiner* — Julian W Woo
(74) *Attorney, Agent, or Firm* — Innovation Counsel LLP

(57) ABSTRACT

One embodiment is directed to a system for deploying a device to a distal location across a vessel, comprising an elongate introducer sheath tubing member comprising open-cell fibrous wall material defining a lumen therethrough, wherein in a collapsed configuration the sheath has a first cross-sectional outer diameter and a first lumen inner diameter, and in an expanded configuration, the sheath has a second cross-sectional outer diameter and a second lumen inner diameter; and a substantially non-porous expandable layer coupled to a proximal portion of sheath and configured to prevent fluids present in the lumen from crossing the fibrous wall material. Also disclosed is a delivery assembly comprising an obturator which releasably captures the distal portion of an introducer sheath which obturator can be removed after the sheath is deployed to a desired location.

19 Claims, 29 Drawing Sheets

Related U.S. Application Data application No. 13/673,898, filed on Nov. 9, 2012, now Pat. No. 10,959,844, and a continuation-in-part of application No. 13/673,911, filed on Nov. 9, 2012, now Pat. No. 9,370,438, application No. 14/934,767, which is a continuation-in-part of application No. 14/274,563, filed on May 9, 2014, now Pat. No. 9,545,298.

(60) Provisional application No. 61/717,575, filed on Oct. 23, 2012, provisional application No. 61/558,397, filed on Nov. 10, 2011, provisional application No. 61/558,357, filed on Nov. 10, 2011, provisional application No. 61/824,471, filed on May 17, 2013, provisional application No. 61/822,204, filed on May 10, 2013.

(51) Int. Cl.
| | | |
|---|---|---|
| *A61F 2/24* | (2006.01) | |
| *A61L 29/14* | (2006.01) | |
| *A61M 39/06* | (2006.01) | |
| *A61M 25/06* | (2006.01) | |
| *A61M 25/00* | (2006.01) | |
| *A61M 29/00* | (2006.01) | |

(52) U.S. Cl.
CPC .......... *A61F 2/2436* (2013.01); *A61L 29/14* (2013.01); *A61M 25/0662* (2013.01); *A61M 29/00* (2013.01); *A61M 2025/0024* (2013.01); *A61M 2039/0626* (2013.01)

(58) Field of Classification Search
CPC ....... A61M 2025/0675–0687; A61M 25/0045; A61M 2025/0046; A61M 2025/0681; A61M 2025/0687; A61M 29/00; A61M 2039/0626; A61B 17/3431–3439; A61B 17/3468; A61B 2017/3433; A61B 17/3498; A16F 2/2427–2439; A16F 2/2436; A61L 29/14; A61F 2/2436
See application file for complete search history.

(56) References Cited

U.S. PATENT DOCUMENTS

| | | | |
|---|---|---|---|
| 4,954,126 A | 9/1990 | Wallsten | |
| 5,061,275 A | 10/1991 | Wallsten et al. | |
| 5,064,414 A * | 11/1991 | Revane | A61M 25/0612 604/165.01 |
| 5,221,261 A | 6/1993 | Termin et al. | |
| 5,290,295 A * | 3/1994 | Querals | A61M 25/104 604/264 |
| 5,415,664 A * | 5/1995 | Pinchuk | A61F 2/95 604/523 |
| 5,431,676 A * | 7/1995 | Dubrul | A61B 17/3439 604/164.1 |
| 5,527,282 A | 6/1996 | Segal | |
| 5,863,366 A * | 1/1999 | Snow | A61B 17/12022 156/143 |
| 5,911,702 A * | 6/1999 | Romley | A61B 17/3439 604/171 |
| 5,941,896 A | 8/1999 | Kerr | |
| 5,997,508 A | 12/1999 | Lunn et al. | |
| 6,090,072 A * | 7/2000 | Kratoska | A61B 17/3439 604/164.01 |
| 6,179,851 B1 | 1/2001 | Barbut et al. | |
| 6,692,462 B2 * | 2/2004 | Mackenzie | A61B 17/3415 604/104 |
| 6,706,033 B1 | 3/2004 | Martinez et al. | |
| 7,014,647 B2 | 3/2006 | Brady et al. | |
| 7,766,820 B2 | 8/2010 | Core | |
| 8,206,280 B2 | 6/2012 | Evans et al. | |
| 8,591,539 B2 | 11/2013 | Gellman | |
| 8,900,214 B2 * | 12/2014 | Nance | A61B 17/3439 604/509 |
| 9,370,438 B2 | 6/2016 | Ginn | |
| 9,545,298 B2 | 1/2017 | Ginn et al. | |
| 9,555,214 B2 | 1/2017 | Ren et al. | |
| 10,179,048 B2 | 1/2019 | Marchand et al. | |
| 2001/0041919 A1 | 11/2001 | Tsugita et al. | |
| 2001/0053929 A1 | 12/2001 | Vonesh et al. | |
| 2002/0016564 A1 | 2/2002 | Courtney et al. | |
| 2002/0077596 A1 | 6/2002 | McKenzie et al. | |
| 2002/0077598 A1 | 6/2002 | Yap et al. | |
| 2003/0050658 A1* | 3/2003 | Trask | A61M 25/0606 606/191 |
| 2003/0144670 A1* | 7/2003 | Pavcnik | A61F 2/2436 606/108 |
| 2004/0153117 A1 | 8/2004 | Clubb et al. | |
| 2004/0215167 A1 | 10/2004 | Belson | |
| 2004/0260331 A1 | 12/2004 | D'aquanni et al. | |
| 2005/0021125 A1 | 1/2005 | Stack et al. | |
| 2005/0149113 A1 | 7/2005 | Douk et al. | |
| 2005/0216053 A1 | 9/2005 | Douk et al. | |
| 2006/0052750 A1* | 3/2006 | Lenker | A61B 17/3439 604/164.01 |
| 2006/0271093 A1 | 11/2006 | Holman et al. | |
| 2006/0282154 A1 | 12/2006 | Oepen et al. | |
| 2007/0016280 A1 | 1/2007 | Yacoby et al. | |
| 2007/0244501 A1 | 10/2007 | Horn et al. | |
| 2008/0167705 A1 | 7/2008 | Agnew | |
| 2008/0188928 A1 | 8/2008 | Salahieh et al. | |
| 2008/0195137 A1 | 8/2008 | Alleyne et al. | |
| 2008/0243068 A1 | 10/2008 | Ramzipoor | |
| 2009/0005675 A1 | 1/2009 | Grunwald et al. | |
| 2009/0024202 A1 | 1/2009 | Dave et al. | |
| 2009/0137900 A1 | 5/2009 | Bonner et al. | |
| 2009/0182278 A1 | 7/2009 | Eversull | |
| 2009/0182360 A1 | 7/2009 | Makower | |
| 2009/0240202 A1* | 9/2009 | Drasler | A61M 25/0023 604/164.03 |
| 2009/0254169 A1 | 10/2009 | Spenser et al. | |
| 2009/0287182 A1* | 11/2009 | Bishop | A61M 25/0662 604/509 |
| 2010/0094392 A1 | 4/2010 | Nguyen et al. | |
| 2010/0100167 A1 | 4/2010 | Bortlein et al. | |
| 2010/0174355 A1 | 7/2010 | Boyle et al. | |
| 2010/0217304 A1 | 8/2010 | Angel et al. | |
| 2010/0234932 A1 | 9/2010 | Arbefeville | |
| 2010/0305604 A1 | 12/2010 | Pah | |
| 2010/0312268 A1 | 12/2010 | Belson | |
| 2011/0015716 A1 | 1/2011 | Silverman | |
| 2011/0022076 A1 | 1/2011 | Lashinski | |
| 2011/0125258 A1 | 5/2011 | Centola | |
| 2011/0257592 A1 | 10/2011 | Ventura et al. | |
| 2012/0083877 A1 | 4/2012 | Nguyen et al. | |
| 2012/0101510 A1 | 4/2012 | Lenker et al. | |
| 2012/0209375 A1 | 8/2012 | Madrid et al. | |
| 2013/0131787 A1 | 5/2013 | Ginn | |
| 2013/0138201 A1 | 5/2013 | Ginn | |
| 2014/0336695 A1 | 11/2014 | Naor | |
| 2014/0336752 A1 | 11/2014 | Ginn et al. | |
| 2015/0165158 A1* | 6/2015 | Ren | A61M 25/0023 604/264 |
| 2016/0338828 A1 | 11/2016 | Ginn | |

FOREIGN PATENT DOCUMENTS

| | | |
|---|---|---|
| CA | 2855387 A1 | 5/2013 |
| CN | 1204242 A | 1/1999 |
| CN | 104039381 A | 9/2014 |
| EP | 2663355 A1 | 11/2013 |
| EP | 2776114 A1 | 9/2014 |
| EP | 3449969 A1 | 9/2014 |
| EP | 2776114 B1 | 10/2018 |
| FR | 2776114 A1 | 9/1999 |
| FR | 2776114 B1 | 10/2007 |
| JP | H09501594 A | 2/1997 |
| JP | H11509130 A | 8/1999 |
| JP | 2001517973 A | 10/2001 |

(56) References Cited

FOREIGN PATENT DOCUMENTS

| | | |
|---|---|---|
| JP | 2002336261 A | 11/2002 |
| JP | 2006500970 A | 1/2006 |
| JP | 2009529401 A | 8/2009 |
| JP | 2013-34867 A | 2/2013 |
| JP | 2015500681 A | 1/2015 |
| WO | 95/05207 A2 | 2/1995 |
| WO | 97/21403 A1 | 6/1997 |
| WO | 98/09678 A1 | 3/1998 |
| WO | 99/24102 A1 | 5/1999 |
| WO | 01/91844 A1 | 6/2001 |
| WO | 02/056955 | 7/2002 |
| WO | 02/056955 A1 | 7/2002 |
| WO | 03/090834 A2 | 11/2003 |
| WO | 2007/106755 A1 | 9/2007 |
| WO | 2009/131612 A1 | 10/2009 |
| WO | 2010045297 A2 | 4/2010 |
| WO | 2010105195 A2 | 9/2010 |
| WO | 2011/096975 A1 | 8/2011 |
| WO | 2013/037505 | 3/2013 |
| WO | 2013037505 A1 | 3/2013 |
| WO | 2013071179 A1 | 5/2013 |

OTHER PUBLICATIONS

Extended European Search Report dated Oct. 28, 2016, International Patent Application No. PCT/US14/037924 with International Filing Date of May 13, 2014 (9 Pages).

"U.S. Appl. No. 13/673,898, Advisory Action dated Jul. 31, 2017", 3 pgs.

"U.S. Appl. No. 13/673,898, Advisory Action dated Aug. 5, 2016", 5 pgs.

"U.S. Appl. No. 13/673,898, Appeal Brief filed Jul. 19, 2017", 19 pgs.

"U.S. Appl. No. 13/673,898, Appeal Brief filed Aug. 9, 2017", 2 pgs.

"U.S. Appl. No. 13/673,898, Appeal Decision mailed Dec. 27, 2019", 26 pgs.

"U.S. Appl. No. 13/673,898, Examiner's Answer to Appeal Brief mailed Dec. 19, 2017", 12 pgs.

"U.S. Appl. No. 13/673,898, Final Office Action dated Apr. 20, 2017", 20 pgs.

"U.S. Appl. No. 13/673,898, Final Office Action dated May 25, 2016", 10 pgs.

"U.S. Appl. No. 13/673,898, Non Final Office Action dated Sep. 14, 2015", 11 pgs.

"U.S. Appl. No. 13/673,898, Non Final Office Action dated Nov. 16, 2016", 16 pgs.

"U.S. Appl. No. 13/673,898, Notice of Non-Complaint Appeal Brief mailed Aug. 2, 2017", 2 pgs.

"U.S. Appl. No. 13/673,898, Reply Brief filed Jan. 30, 2018", 9 pgs.

"U.S. Appl. No. 13/673,898, Response filed Feb. 5, 2016 to Non Final Office Action dated Sep. 14, 2015", 8 pgs.

"U.S. Appl. No. 13/673,898, Response filed Jun. 2, 2017 to Final Office Action dated Apr. 20, 2017", 6 pgs.

"U.S. Appl. No. 13/673,898, Response filed Jun. 14, 2016 to Final Office Action dated May 25, 2016", 10 pgs.

"U.S. Appl. No. 13/673,898, Response filed Aug. 7, 2015 to Restriction Requirement dated Mar. 20, 2015", 5 pgs.

"U.S. Appl. No. 13/673,898, Response filed Aug. 8, 2016 to Advisory Action dated Aug. 5, 2016", 10 pgs.

"U.S. Appl. No. 13/673,898, Response filed Dec. 22, 2016 to Non Final Office Action dated Nov. 16, 2016", 11 pgs.

"U.S. Appl. No. 13/673,898, Restriction Requirement dated Mar. 20, 2015", 6 pgs.

"U.S. Appl. No. 13/673,911, Advisory Action dated Feb. 16, 2016", 3 pgs.

"U.S. Appl. No. 13/673,911, Final Office Action dated Dec. 18, 2015", 6 pgs.

"U.S. Appl. No. 13/673,911, Non Final Office Action dated Apr. 6, 2015", 11 pgs.

"U.S. Appl. No. 13/673,911, Notice of Allowance dated Mar. 11, 2016", 9 pgs.

"U.S. Appl. No. 13/673,911, Response filed Jan. 28, 2016 to Final Office Action dated Dec. 18, 2015", 8 pgs.

"U.S. Appl. No. 13/673,911, Response filed Mar. 1, 2016 to Advisory Action dated Feb. 16, 2016", 7 pgs.

"U.S. Appl. No. 13/673,911, Response filed Sep. 8, 2015 to Non Final Office Action dated Apr. 4, 2015", 7 pgs.

"U.S. Appl. No. 14/274,563, 312 Amendment filed Aug. 9, 2016", 4 pgs.

"U.S. Appl. No. 14/274,563, 312 Amendment filed Aug. 12, 2016", 3 pgs.

"U.S. Appl. No. 14/274,563, Advisory Action dated Jun. 3, 2016", 3 pgs.

"U.S. Appl. No. 14/274,563, Final Office Action dated Mar. 28, 2016", 19 pgs.

"U.S. Appl. No. 14/274,563, Non Final Office Action dated Jun. 3, 2015", 15 pgs.

"U.S. Appl. No. 14/274,563, Non Final Office Action dated Sep. 8, 2014", 7 pgs.

"U.S. Appl. No. 14/274,563, Notice of Allowance dated Aug. 8, 2016", 11 pgs.

"U.S. Appl. No. 14/274,563, PTO Response to Rule 312 Communication dated Sep. 26, 2016", 2 pgs.

"U.S. Appl. No. 14/274,563, Response filed Feb. 9, 2015 to Non Final Office Action dated Sep. 8, 2014", 13 pgs.

"U.S. Appl. No. 14/274,563, Response filed Apr. 29, 2016 to Final Office Action dated Mar. 28, 2016", 9 pgs.

"U.S. Appl. No. 14/274,563, Response filed Jun. 15, 2016 to Advisory Action dated Jun. 3, 2016", 9 pgs.

"U.S. Appl. No. 14/274,563, Response filed Oct. 20, 2015 to Non Final Office Action dated Jun. 3, 2015", 11 pgs.

"U.S. Appl. No. 15/228,380, Final Office Action dated Nov. 14, 2018", 8 pgs.

"U.S. Appl. No. 15/228,380, Non Final Office Action dated Apr. 20, 2018", 7 pgs.

"U.S. Appl. No. 15/228,380, Non Final Office Action dated Jun. 26, 2019", 8 pgs.

"U.S. Appl. No. 15/228,380, Response filed Feb. 14, 2019 to Final Office Action dated Nov. 14, 2018", 6 pgs.

"U.S. Appl. No. 15/228,380, Response filed Jun. 26, 2018 to Non Final Office Action dated Apr. 20, 2018", 7 pgs.

"U.S. Appl. No. 15/228,380, Response filed Oct. 24, 2019 to Non-Final Office Action dated Jun. 26, 2019", 7 pgs.

"Australian Application Serial No. 2012335016, First Examiner Report dated Jul. 17, 2016", 3 pgs.

"Australian Application Serial No. 2012335016, Response filed Jan. 12, 2017 to First Examiner Report dated Jul. 17, 2016", 17 pgs.

"Australian Application Serial No. 2012335016, Response filed Apr. 12, 2017 to Second Examiner Report dated Feb. 20, 2017", 8 pgs.

"Australian Application Serial No. 2012335016, Response filed Jun. 29, 2017 to Third Examiner Report dated Jun. 12, 2017", 11 pgs.

"Australian Application Serial No. 2012335016, Second Examiner Report dated Feb. 20, 2017", 3 pgs.

"Australian Application Serial No. 2012335016, Third Examiner Report dated Jun. 12, 2017", 4 pgs.

"Canadian Application Serial No. 2,855,387, Office Action dated Jun. 12, 2018", 4 pgs.

"Canadian Application Serial No. 2,855,387, Office Action dated Mar. 8, 2019", 4 pgs.

"Canadian Application Serial No. 2,855,387, Response filed Sep. 6, 2019 to Office Action dated Mar. 8, 2019", 78 pgs.

"Canadian Application Serial No. 2,855,387, Response filed Dec. 12, 2018 to Office Action dated Jun. 12, 2018", 27 pgs.

"Canadian Application Serial No. 2,855,387, Voluntary Amendment filed Oct. 29, 2019", 14 pgs.

"Chinese Application Serial No. 201280066517.X, Office Action dated Oct. 26, 2015", 17 pgs.

"European Application Serial No. 12847961.5, Communication Pursuant to Article 94(3) EPC dated Mar. 29, 2016", 5 pgs.

"European Application Serial No. 12847961.5, Communication Pursuant to Article 94(3) EPC dated Aug. 17, 2017", 6 pgs.

(56) References Cited

OTHER PUBLICATIONS

"European Application Serial No. 12847961.5, Communication Pursuant to Article 94(3) EPC dated Nov. 15, 2016", 5 pgs.
"European Application Serial No. 12847961.5, Extended European Search Report dated May 22, 2015", 8 pgs.
"European Application Serial No. 12847961.5, Intention to Grant dated Apr. 26, 2018", 95 pgs.
"European Application Serial No. 12847961.5, Intention to Grant dated Sep. 17, 2018", 95 pgs.
"European Application Serial No. 12847961.5, Response filed Jan. 2, 2015 to Communication Pursuant to Rules 161(1) and 162 EPC dated Jun. 23, 2014", 11 pgs.
"European Application Serial No. 12847961.5, Response filed May 24, 2017 to Communication Pursuant to Article 94(3) EPC dated Nov. 15, 2016", 52 pgs.
"European Application Serial No. 12847961.5, Response filed Sep. 5, 2018 to Intention to Grant dated Apr. 26, 2018", 8 pgs.
"European Application Serial No. 12847961.5, Response filed Oct. 10, 2016 to Communication Pursuant to Article 94(3) EPC dated Mar. 29, 2016", 13 pgs.
"European Application Serial No. 12847961.5, Response filed Dec. 21, 2015 to Extended European Search Report dated May 22, 2015", 12 pgs.
"European Application Serial No. 12847961.5, Response filed Dec. 29, 2017 to Communication Pursuant to Article 94(3) EPC dated Aug. 17, 2017", 52 pgs.
"European Application Serial No. 18201608.9, Extended European Search Report dated Feb. 1, 2019", 10 pgs.
"International Application Serial No. PCT/US2012/064540, International Preliminary Report on Patentability dated May 22, 2014", 11 pgs.
"International Application Serial No. PCT/US2012/064540, International Search Report dated Feb. 6, 2013", 2 pgs.
"International Application Serial No. PCT/US2012/064540, Written Opinion dated Feb. 6, 2013", 9 pgs.
"International Application Serial No. PCT/US2014/037580, International Preliminary Report on Patentability dated Nov. 19, 2015", 8 pgs.
"Israel Application Serial No. 232542, Office Action dated Sep. 4, 2018", w/o English Translation, 5 pgs.
"Israel Application Serial No. 232542, Office Action dated Sep. 18, 2017", w/o English Translation, 3 pgs.
"Israel Application Serial No. 232542, Response filed Jan. 18, 2018 to Office Action dated Sep. 18, 2017", 2 pgs.
"Israel Application Serial No. 232542, Response filed Dec. 16, 2018 to Office Action dated Sep. 4, 2018", 2 pgs.
"Japanese Application Serial No. 2014-541354, Notice of Reason for Rejection dated Jul. 28, 2016", w/ English Translation, 22 pgs.
EP Application No. 20200790.2, Extended European Search Report, dated Feb. 5, 2021, 7 pages.
JP Application No. 2020-038658, Japanese Office Action, dated Sep. 27, 2021, 4 pages.

\* cited by examiner

202 — Preoperative diagnostics and patient preparation

204 — Establish vascular access (such as by surgically creating an arteriotomy) and insert guidewire

228 — Temporarily apply compression/push loading to elongate loading member (such as a pushwire or pushrod) operatively coupled to a distal portion of an expandable introducer, comprising open-cell braided fiber assembly defining introducer lumen through which dilator assembly may be positioned, to tension a portion of the braided fiber assembly and thereby decrease the overall diameter of the introducer assembly

230 — Insert collapsed/tensioned form of expandable introducer assembly

208 — Remove dilator assembly while leaving guidewire in place through introducer lumen

218 — Insert tubular liner member to occupy at least a portion of the introducer lumen and form a liner member lumen

220 — Insert interventional tools and/or prostheses through the liner member lumen and conduct procedure

222 — Remove interventional tools through the liner member lumen after procedure has been completed

224 — Withdraw tubular liner member from introducer lumen to allow braided fiber assembly to more completely collapse

214 — Withdraw introducer assembly and guidewire proximally through vascular access port

216 — Close vascular access with procedure complete

FIG. 9

202 — Preoperative diagnostics and patient preparation

204 — Establish vascular access (such as by surgically creating an arteriotomy) and insert guidewire 228 — Temporarily apply compression/push loading to elongate loading member (such as a pushwire or pushrod) operatively coupled to a distal portion of an expandable introducer, comprising open-cell braided fiber assembly defining introducer lumen through which dilator assembly may be positioned, to tension a portion of the braided fiber assembly and thereby decrease the overall diameter of the introducer assembly 230 — Insert collapsed/tensioned form of expandable introducer assembly 232 — Remove two-part dilator assembly while leaving guidewire in place through introducer lumen 226 — Temporarily apply tension to elongate loading member (such as a pullwire) operatively coupled to a distal portion of the braided fiber assembly to compress a portion of the braided fiber assembly and thereby increase the diameter of the introducer lumen 210 — Insert interventional tools and/or prostheses through the introducer lumen and conduct procedure; introducer open-cell braided fiber assembly expands to expanded form as tools and/or prostheses are pushed through the introducer lumen 212 — Remove interventional tools through the introducer lumen after procedure has been completed; introducer open-cell braided fiber assembly is allowed to passively contract back toward contracted form 214 — Withdraw introducer assembly and guidewire proximally through vascular access port 216 — Close vascular access with procedure complete.

FIG. 11

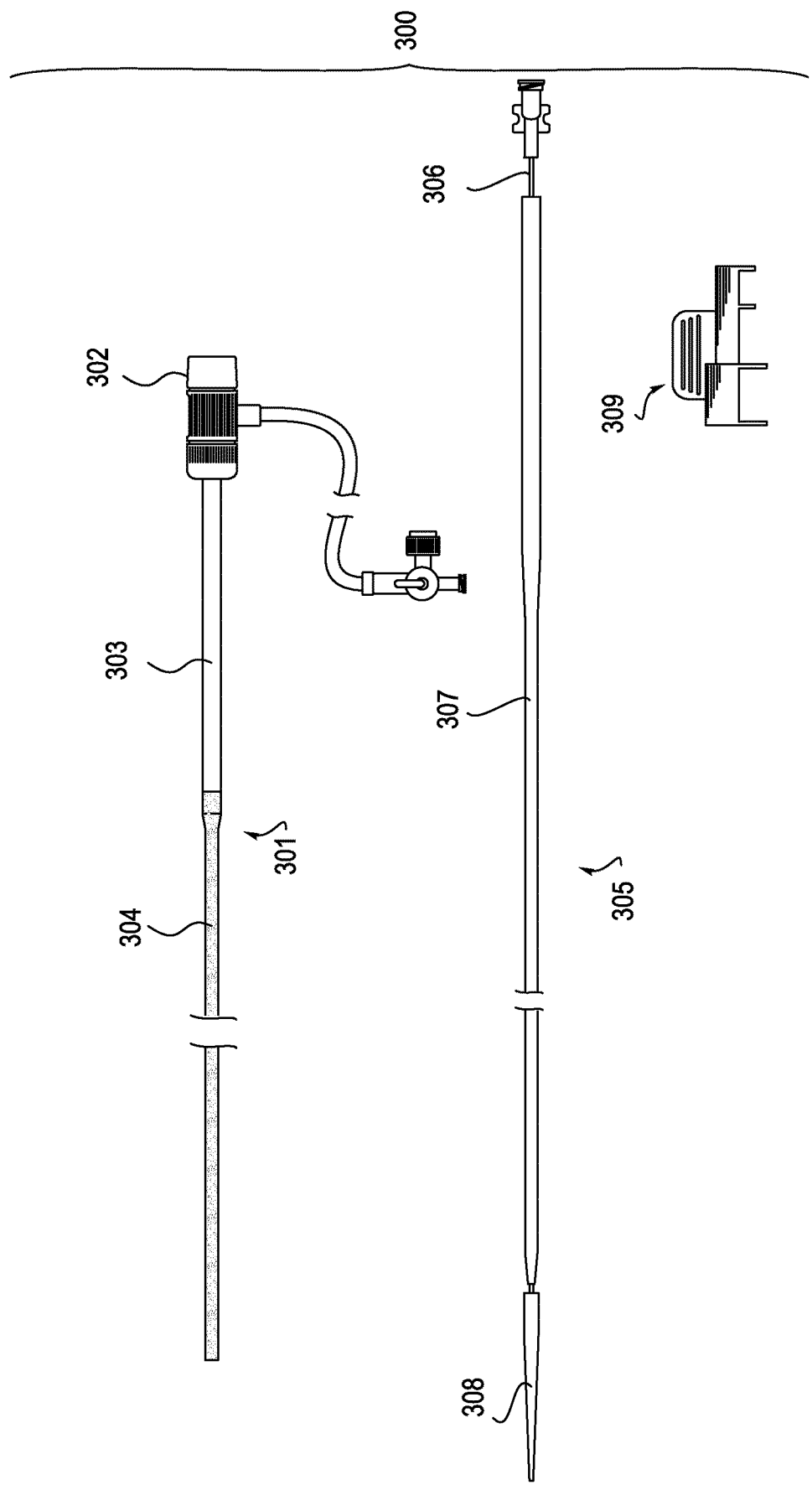

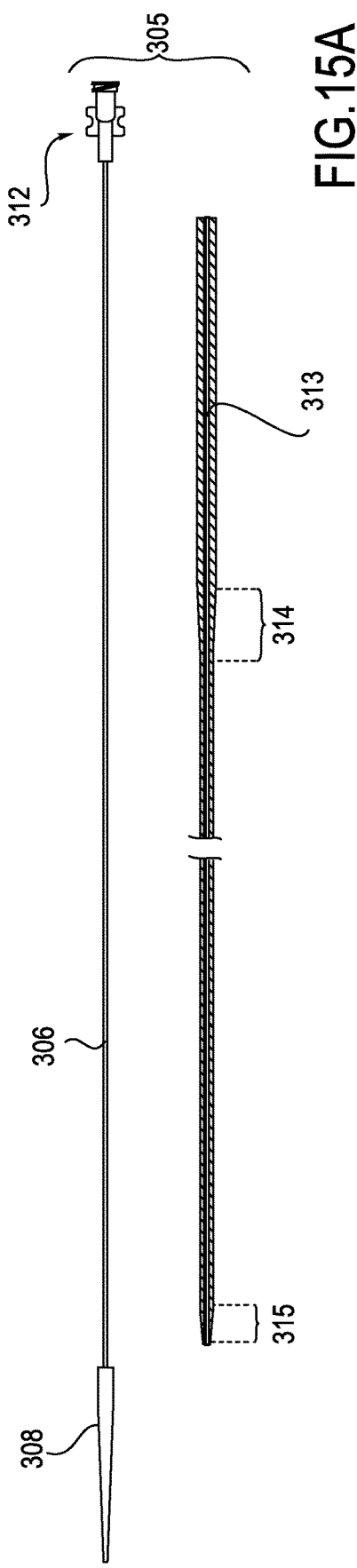
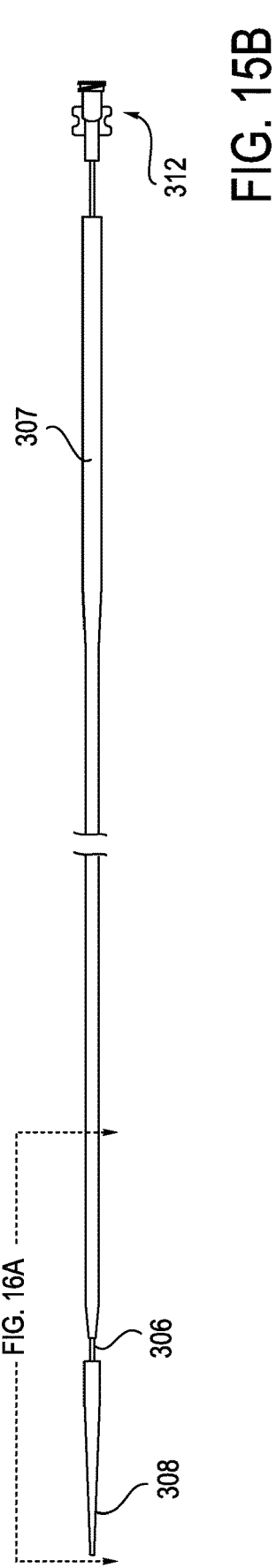
FIG. 15A
FIG. 15B

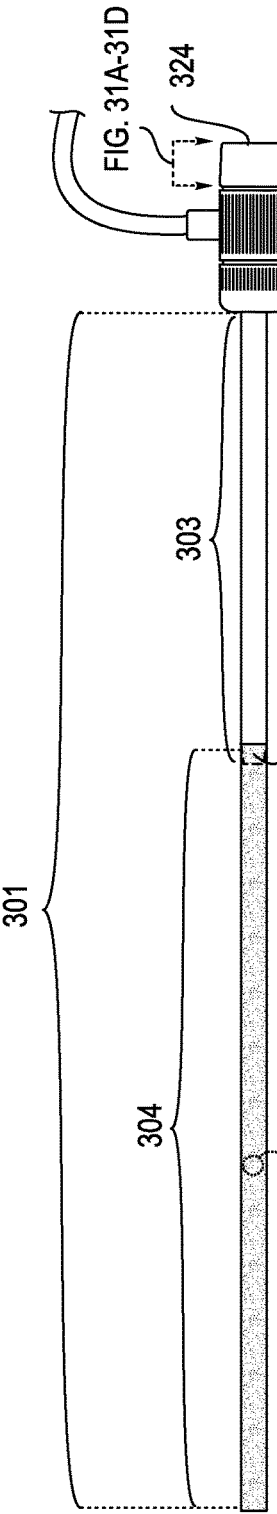
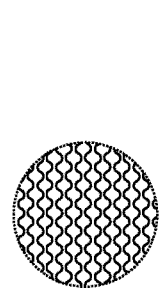
FIG. 17
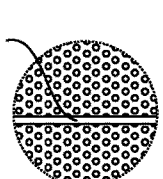
FIG. 18E
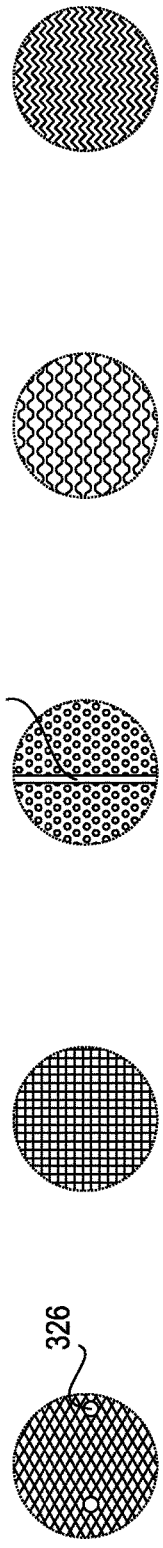
FIG. 18D
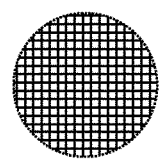
FIG. 18C
FIG. 18B
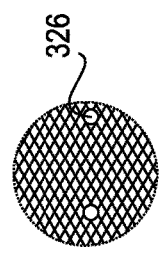
FIG. 18A
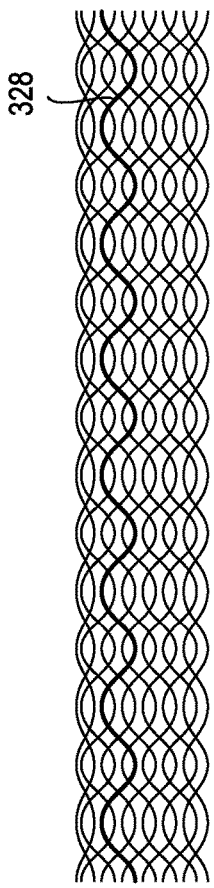
FIG. 18F

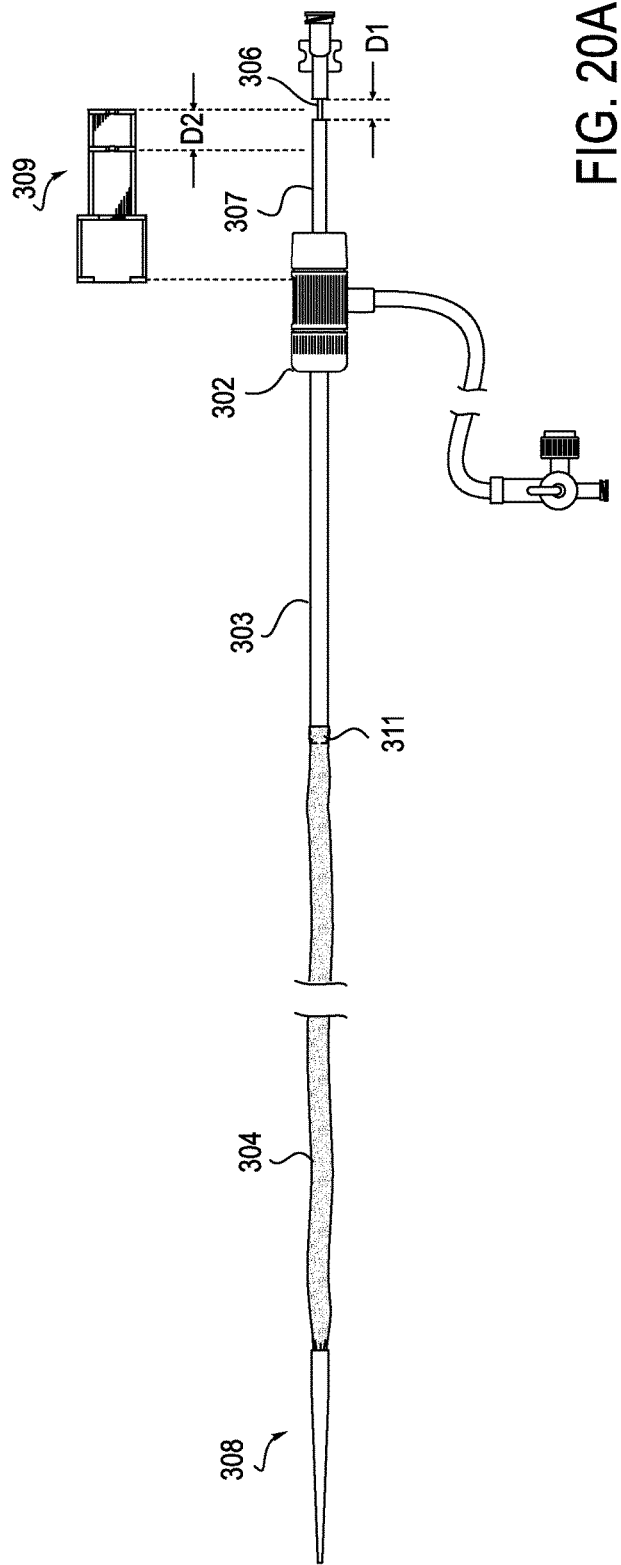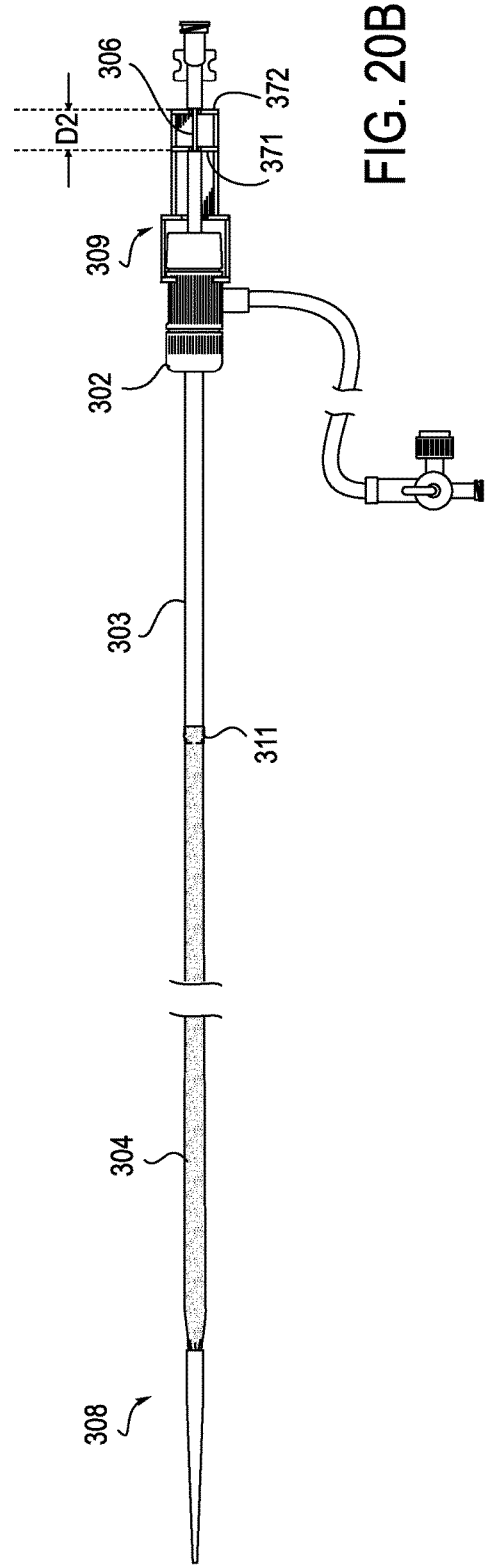

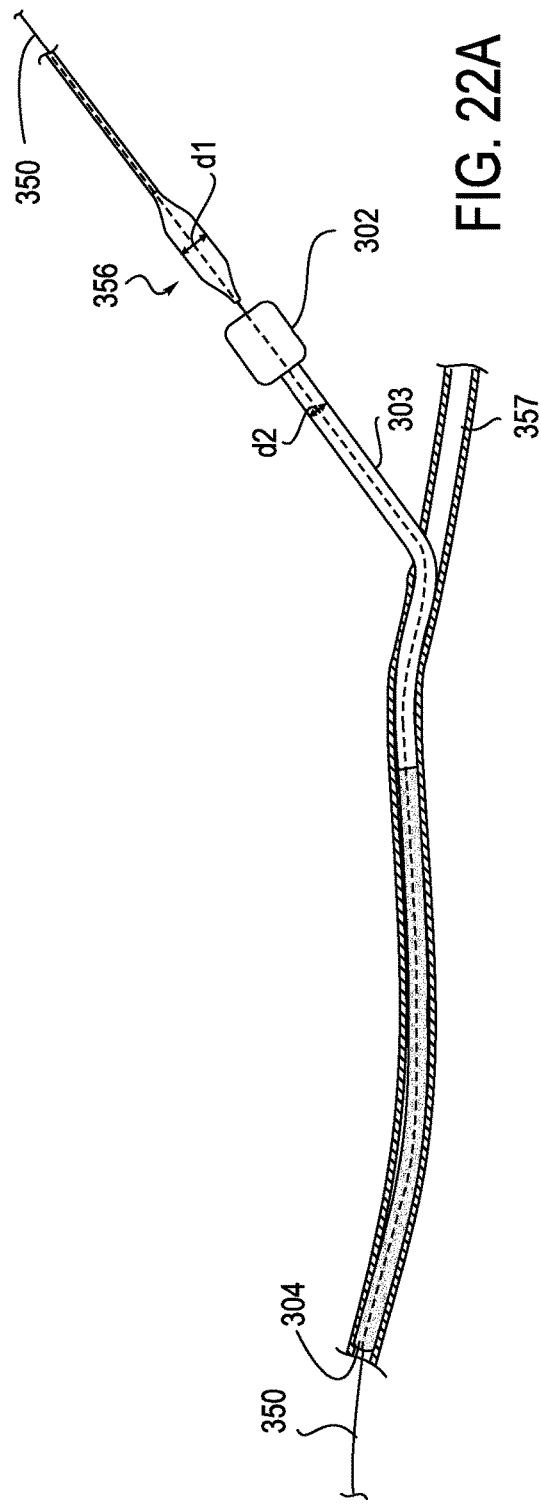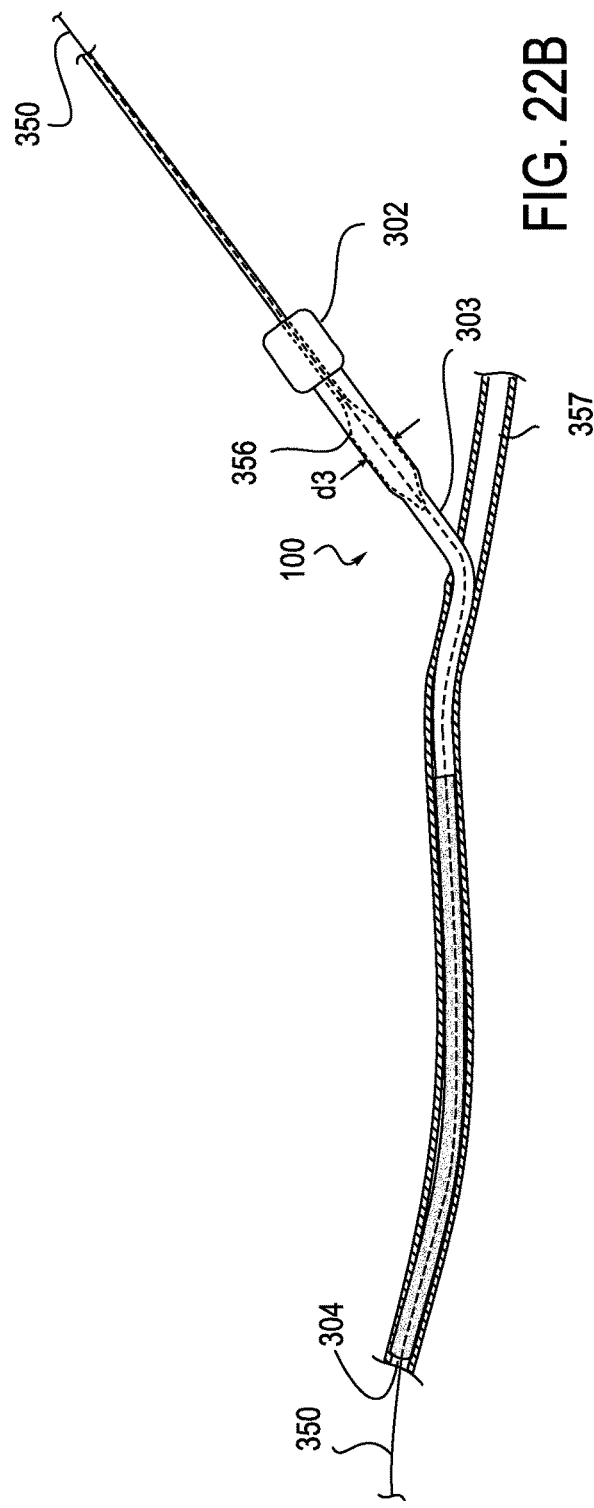

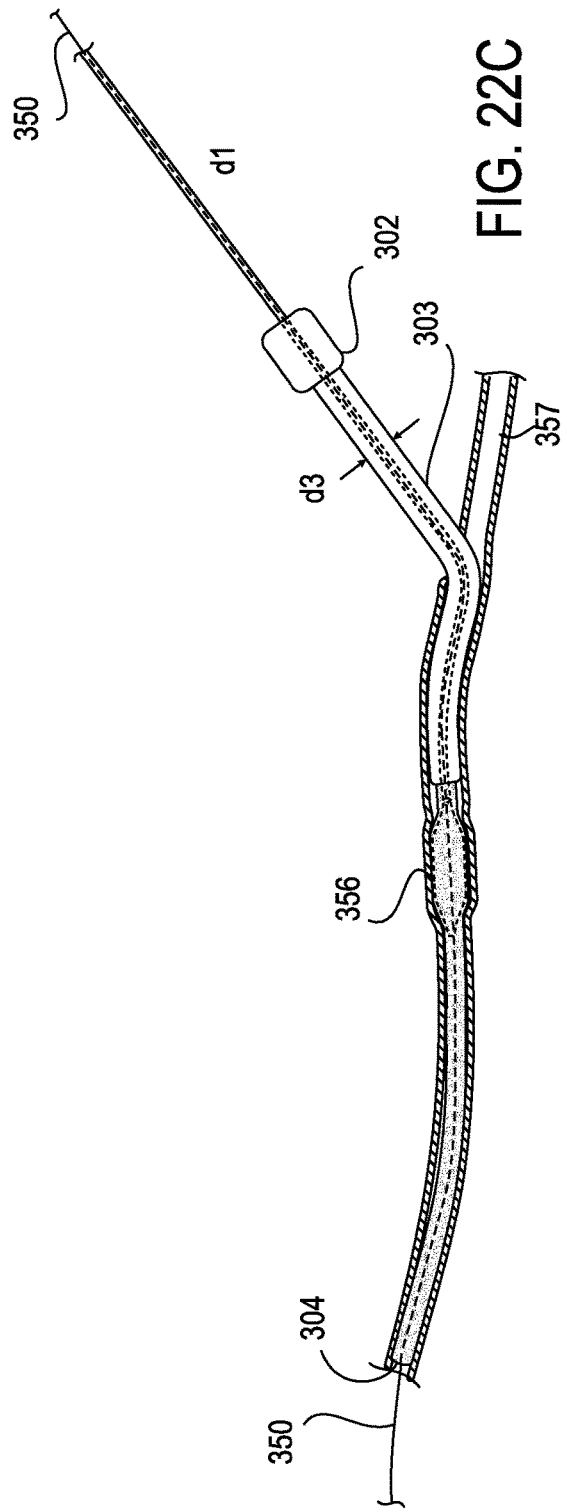
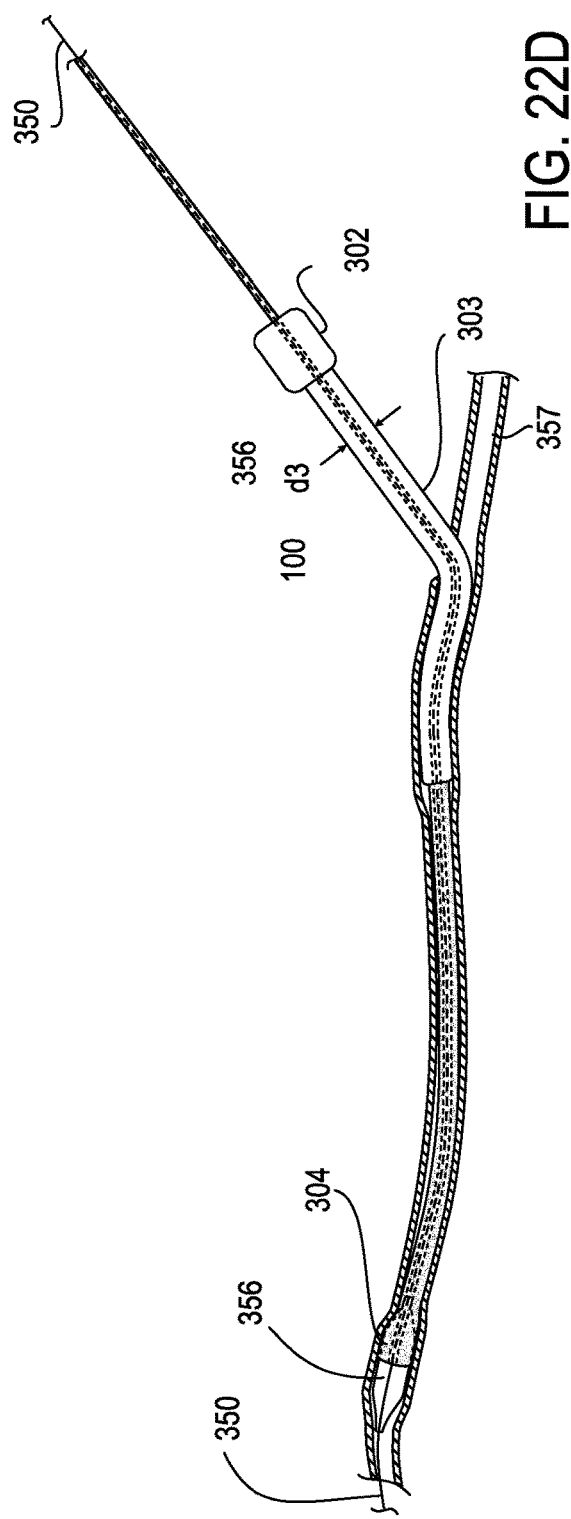

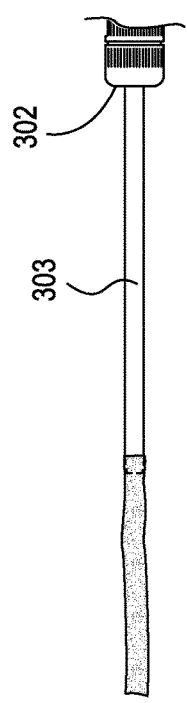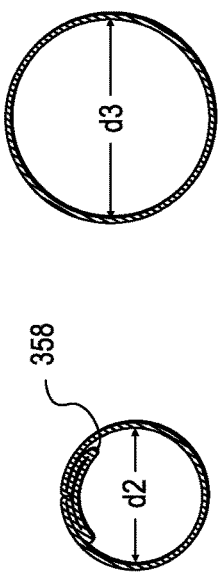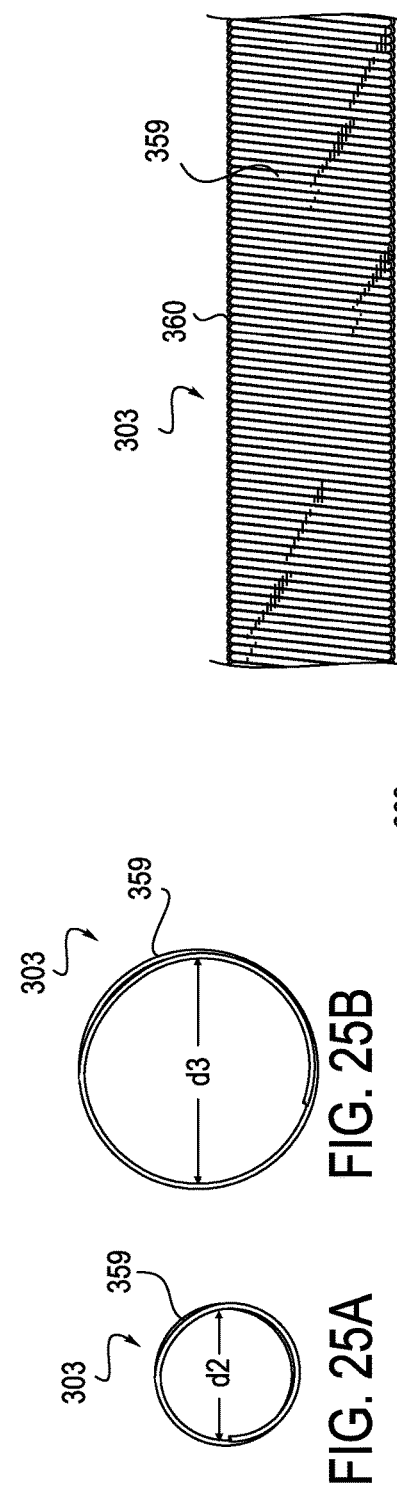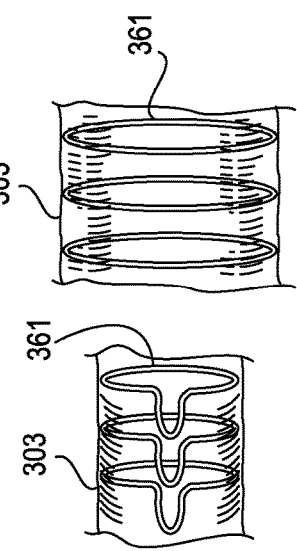

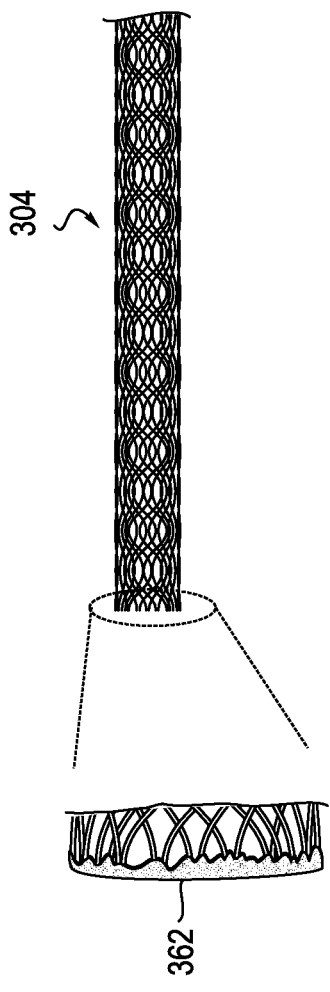
FIG. 28
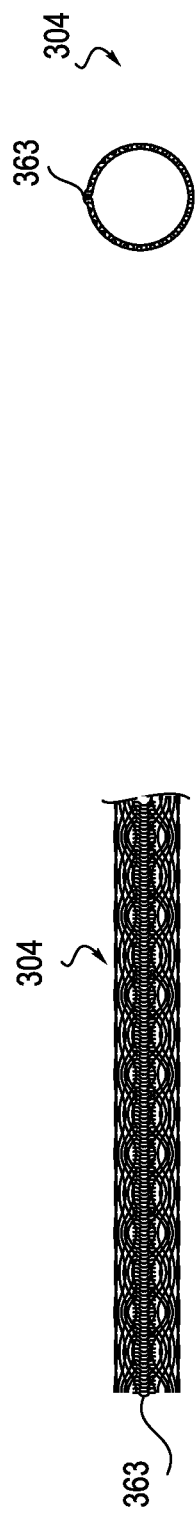
FIG. 29A
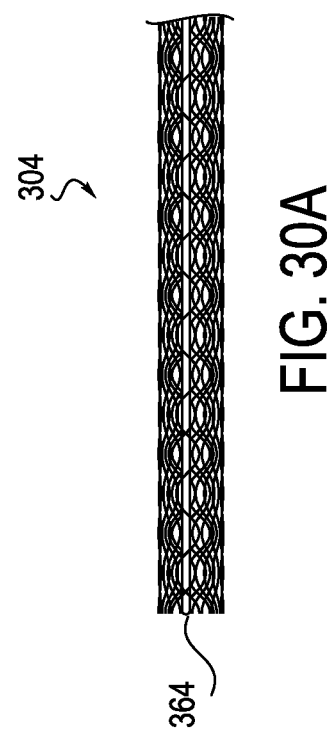
FIG. 29B
FIG. 30A
FIG. 30B

EXPANDABLE INTRODUCER SHEATH AND METHOD

RELATED APPLICATION DATA

The present application is a continuation-in-part of and claims the benefit under 35 U.S.C. § 120 of co-pending U.S. patent application Ser. No. 14/276,952, filed May 13, 2014, which claims the benefit of U.S. Provisional Application Ser. No. 61/824,471, and of Ser. No. 13/673,898, filed Nov. 9, 2012, and Ser. No. 13/673,911, filed Nov. 9, 2012, each of which claim the benefit of U.S. Provisional Patent Application Ser. No. 61/717,575, filed Oct. 23, 2012, 61/558,397, filed Nov. 10, 2011 and 61/558,357 filed Nov. 10, 2011, each of which is incorporated by reference herein in its entirety. The present application also claims the benefit under 35 U.S.C. § 120 of U.S. patent application Ser. No. 14/274,563, filed May 9, 2014, which claims the benefit of U.S. Provisional Application Ser. No. 61/822,204, filed May 10, 2013, each of which is incorporated herein by reference in its entirety.

FIELD OF THE INVENTION

The present invention relates generally to medical interventions conducted through vessels such as the major arteries, and more particularly to access and deployment configurations for conducting percutaneous procedures such as percutaneous valve replacement wherein an introducer sheath may be utilized to provide minimally-invasive vascular access for passing instruments, prostheses, and other structures.

BACKGROUND

Gaining access to the heart and other parts of the cardiovascular anatomy is a continued challenge in cardiovascular medicine. For example, conventional open-surgical procedures for accomplishing tasks such as valve replacement generally involve a thoracotomy and/or creation of one or more access ports across the wall of the heart itself, which is relatively highly invasive and therefore undesirable. Recent progress has been made in the area of catheter-based percutaneous intervention, wherein instrumentation, such as catheters, guidewires, and prostheses, are brought to the heart, brain, or other tissue structures associated with the cardiovascular system through the vessels connected to such structures. These vascular pathways may be quite tortuous and geometrically small, and thus one of the challenges with percutaneous procedures lies in gaining access, conducting the desired interventional and/or diagnostic procedures, and removing the pertinent instrumentation, without damaging the vasculature or associated anatomy. Conventionally with percutaneous procedures, introducer and dilator sets such as that (2) depicted in FIG. 1, have been utilized to provide a usable access conduit through an arteriotomy or other surgical access to the vasculature. For procedures on large, relatively straight, and relatively undiseased vessels, such configurations may be adequate, but frequently cardiovascular diagnostic and/or interventional procedures are conducted on diseased cardiovascular systems and in tortuous anatomy. There is a need for better access tools and procedures, which may be utilized to establish vascular access in a relatively efficient geometric package (ie., in a collapsed state), be expanded in situ as necessary to pass instrumentation, prostheses, or other structures (for example, the un-expanded delivery size of a. CoreValve® aortic valve prosthesis available from Medtronic, Inc. is approximately 18 French; the un-expanded delivery size of a Sapien® valve available from Edwards Lifesciences, Inc. is between 18 and 24 French, depending upon which size is utilized), and to be re-collapsed before or during withdrawal so that the associated anatomy is not undesirably loaded or damaged during such withdrawal.

Such outer sizes do not allow for a conventional guide catheter to be inserted as a protective layer between the tools and the tissue, and therefore the standard of care has become direct insertion of the valve instrumentation through the diseased vessels to reach the target location within or adjacent to the heart. Another complicating factor with such interventions is the fact that it is likely that the aorta through which the devices will be advanced will be diseased (one recent study concluded that 61% of patients over 65 years of age will severe aortic valve stenosis also have severe aortic atherosclerosis; Osrandek, et al., American Journal of Cardiology, 2009; 103:713-717). This complicated surgical paradigm has led some clinical researchers to believe that elevated stroke rates associated with such procedures may be related to the physical insertion of large interventional tools through the diseased vessels and concomitant scraping or micro-scraping action of the tools against the diseased vessel walls, which results in breaking portions of plaque loose and allowing these to flow with the blood stream into the brain and other undesirable landing places. There is a need for a configuration where a relatively thin, but protective sheath-like member can be put in place to guide the interventional tools and prosthesis while mitigating load concentrations and/or scraping or abrasion of the interior of the subject vessels. Various embodiments of the subject invention address these challenges with expandable introducer sheath configurations.

SUMMARY

One embodiment of the present invention is directed to improving hemostasis at the access site of an expandable introducer sheath in a blood vessel. Other embodiments are directed to the proximal region of the expandable introducer sheaths as disclosed in more detail herein. The use of a braid structure as the expandable portion of the sheath in combination with a dilator nose cone is another embodiment of the present invention. In other embodiments, improved radiopacity structure and improved shape stability structures are provided.

Such embodiments are directed to a system for deploying a device to a distal location across a vessel, comprising an elongate introducer sheath tubing member comprising open-cell fibrous wall material defining a lumen therethrough, wherein in a collapsed configuration the sheath has a first cross-sectional outer diameter and a first lumen inner diameter, and in an expanded configuration, the sheath has a second cross-sectional outer diameter and a second lumen inner diameter; and a substantially non-porous expandable layer coupled to a proximal portion of sheath and configured to prevent fluids present in the lumen from crossing the fibrous wall material. In the collapsed configuration, the sheath may be configured to be advanced across at least a portion of the vessel to a position adjacent the distal location without substantial size interference between the first cross sectional outer diameter of the sheath and an inner diameter profile of a lumen of the vessel. Upon positioning the collapsed configuration to the desired position relative to the distal location, the sheath may be configured to be expanded to the expanded configuration to facilitate passage of one or more relatively large diameter structures through the lumen that are larger in diameter than the first cross sectional outer diameter. Upon completion of passage of the one or more relatively large diameter structures, the sheath may be configured to be collapsed back to the collapsed configuration. The first lumen inner diameter may be equal to between about 0 mm and about 4 mm. The second lumen inner diameter may be equal to between about 4 mm and about 7 mm. The system further may comprise one or more radioopaque markers coupled to the sheath and configured to assist an operator observing fluoroscopy with positioning of the sheath relative to the vessel. The open-cell fibrous wall material may comprise a matrix of fibers. The matrix of fibers may be arranged in a braided pattern. The fibers may comprise a polymeric material. The polymeric material may be selected from the group consisting of: polyester, polyamide, polypropylene, and copolymers thereof. The fibers each may have a diameter of between about 0.003 inches and about 0.015 inches. The matrix of fibers may be configured to function to prevent expansion of the sheath beyond the second cross-sectional outer diameter. The matrix of fibers may be configured to bias the sheath to remain in the collapsed configuration until it is urged into the expanded configuration by passage of a structure through the lumen. The matrix of fibers may be configured to locally expand around the structure passed through the lumen, and then to locally re-collapse as the structure passes to an adjacent portion of the lumen. The substantially non-porous expandable layer may comprise a flexible polymeric material selected from the group consisting of: silicone rubber, olefin block copolymers, and copolymers thereof. The matrix of fibers may define pores across the wall material which have a diameter between about 0.002 inches and about 0.20 inches. The system further may comprise an inner liner member operatively coupled through the lumen of the elongate introducer sheath tubing member to define an inner working lumen, the inner liner member configured to structurally reinforce the tubing member and facilitate relative motion between structures which may be passed through the inner working lumen. The substantially non-porous expandable layer may be configured to extend from a proximal end of the elongate introducer sheath tubing member for a length of about 10 centimeters distally. The device may comprise an implantable prosthesis selected to be passed through the expandable sheath to the distal location across the vessel. The implantable prosthesis may comprise a cardiac valve prosthesis. The matrix of fibers may comprise a mesh pattern. The system further may comprise a tensioning member operatively coupled to at least a portion of the matrix of fibers and configured to maintain such portion in a relaxed configuration, the tensioning member comprising a proximal portion configured to be manually tensioned or relaxed by an operator.

BRIEF DESCRIPTION OF THE DRAWINGS

FIG. 9 illustrates various aspects of a minimally invasive surgical access technique in accordance with the present invention.

FIG. 11 illustrates various aspects of a minimally invasive surgical access technique in accordance with the present invention.

FIG. 13 illustrates an embodiment of the present invention in which the introducer sheath assembly is provided with a proximal portion which is more rigid than the distal portion of the sheath and with a dilator assembly.

FIGS. 15A and 15B illustrate the structure of the dilator assembly of the device illustrated in FIG. 13.

FIG. 17 illustrates an exemplary location for a radiopaque element in the sheath and a hemostatic valve on the hub of the sheath assembly.

FIGS. 18A, 18B, 18C, 18D, 18E and 18F illustrate various mesh configurations.

FIGS. 20A and 20B illustrate, respectively, the mesh of the sheath when not under tension and when under tension.

FIGS. 22A, 22B, 22C and 22D illustrate the sequential movement of a device through the sheath as the device is being deployed.

FIGS. 23, 24A, 24B, 25A, 25B, 26, 27A and 27B illustrate various embodiments of the proximal section of the sheath.

FIGS. 28, 29A, 29B, 30A and 30B illustrate various configurations of the distal section of the sheath.

DETAILED DESCRIPTION

Figure 1:
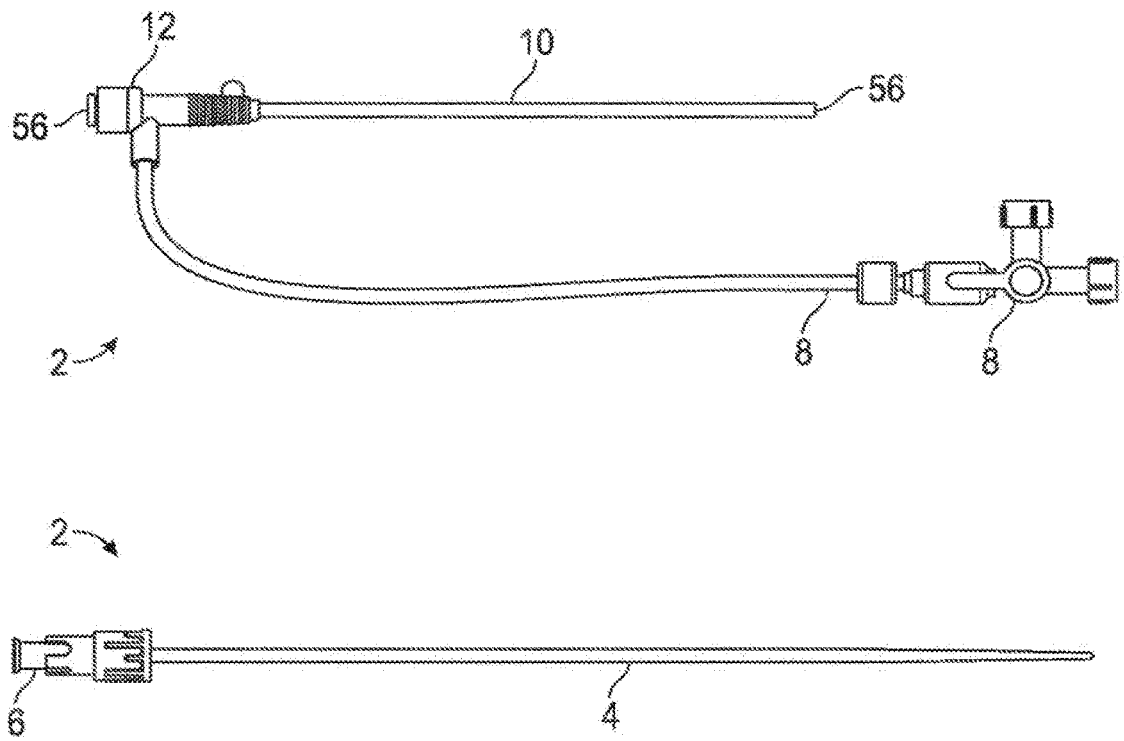
FIG. 1 illustrates various aspects of a conventional introducer and dilator kit for cardiovascular intervention.

Referring again to FIG. 1, a conventional introducer sheath and dilator kit (2) is depicted comprising an elongate dilator (4) with a proximal luer assembly (6); the dilator is configured to be inserted into the working lumen (56) of the introducer sheath through a proximal seal coupled to a hub (12) structure, which is also coupled to an extension tube with stopcock (8), which may be utilized for infusion of fluids into the introducer lumen (56), for example. The conventional introducer sheath will comprise an elongate tubular member (10) coupled proximally to the hub (12) and being made from a relatively non-expandable polymeric material or combination of polymeric materials, which results in introducer sheaths which are selected for their off-the-shelf working lumen (56) diameter (i.e., they generally are not considered to have expandable diametric dimensions). Certain trocars and introducer catheters have been produced with expandable diametric geometries, but they have been limited in their expandability due to the constraints of hoop stress and friction (i.e., with a relatively low-modulus or even rubber-like material, diametric expansion will be at least linearly proportional to hoop stress in the expanded sheath material, which is proportional to frictional loads—which generally results in a useful expandability limit, beyond which too large a load is required to develop relative motion between structures being passed through the working lumen and the sheath which defines the working lumen).

Figure 2A:
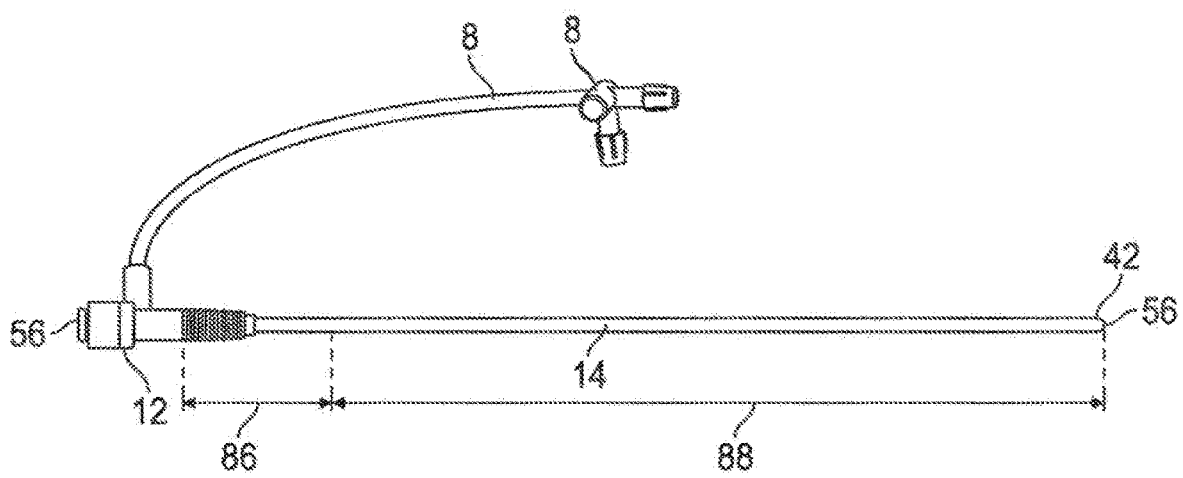
FIGS. 2A, 2B, 2C, 2D, 2E, 2F, 2G, 2H, 2I, 2J, 2K, 2L, 2M, 2N and 2O illustrate various aspects of an inventive expandable introducer sheath that may be used in conducting various cardiovascular procedures.

Referring to FIG. 2A, one embodiment of an expandable introducer sheath to address these challenges is depicted, wherein the introducer sheath tubing member or assembly (14) comprises a plurality of braided fibers arranged in a braided or mesh pattern to form an open-cell fibrous wall material comprising the sheath tubing member, which defines the introducer working lumen (56). In one embodiment the distal portion (88) of the introducer sheath tubing member (14) comprises the open-cell fibrous wall material in its porous form without a nonporous coating, while a portion of the proximal portion (86), such as about the proximal 10 centimeters, of the introducer sheath tubing member (14) is coated with a substantially non-porous expandable layer to assist with preventing bleeding when the sheath is installed in a patient with the proximal portion extending transcutaneously out of the surgically-created wound (such as an arteriotomy).

Figure 2B:
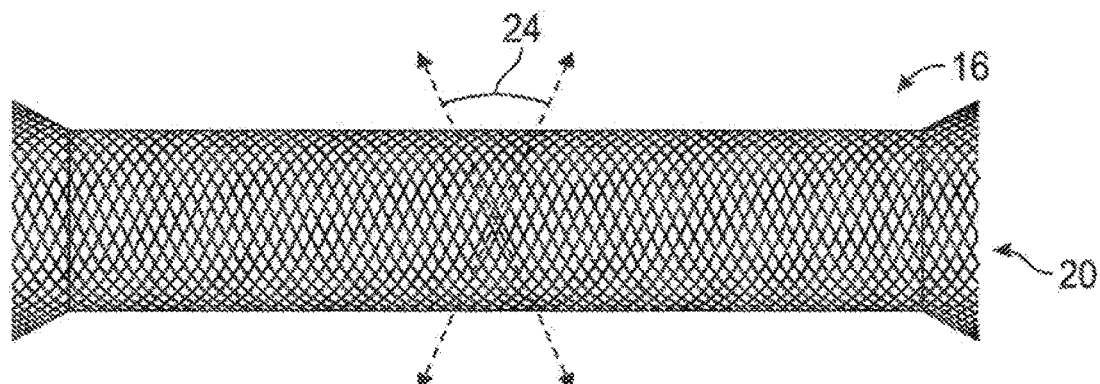
Figure 2C:
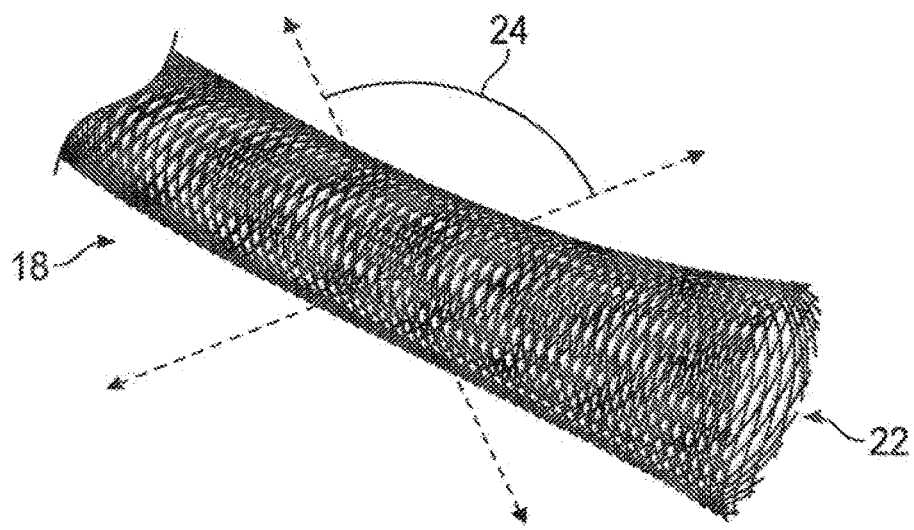
Figure 2D:
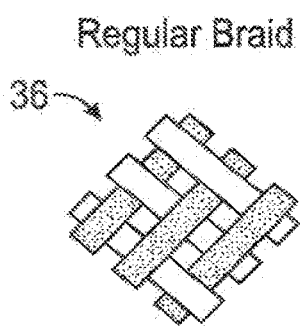
Figure 2E:
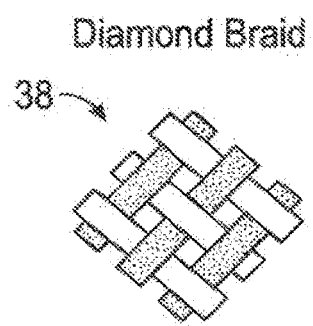
Figure 2F:
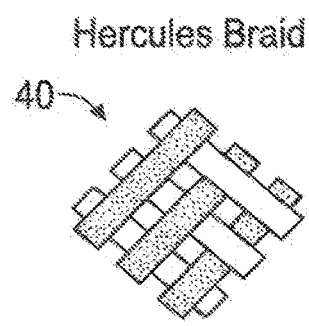

Referring to FIG. 2B, a braiding configuration (16) is depicted wherein single strands (20) of fibrous material are braided with each other, such as in one of the depicted patterns of FIGS. 2D, 2E, or 2F (36, 38, or 40, respectively) to allow for significant diametric expandability and contractibility of the overall fiber/mesh assembly due to available relative motion between the fibers in an open-cell braided configuration. In other words, it is the available micromotion of the fibers of the braided pattern relative to each other that allows for relatively low-load expandability and contractibility of the overall construct. This relative motion may be somewhat decreased when the fibrous assembly is combined with other structures, such as a nonporous coating, which is the reason that in one embodiment, wherein maximum expandability and contractibility is preferred, such nonporous coating is only featured on the proximal aspect, or in another embodiment, not at all (i.e., there is no nonporous coating in such embodiment, and proximal bleedthrough at the percutaneous access site may be mitigated by another means such as gauze compression or a very thin and highly-expandable lubricious sleeve that is not directly coupled to each portion of the surface of the braided assembly, but is essentially looped around the bulk structure only with a light hoop stress). The intersection angle (24) of intersecting fibers within the woven, braided, or mesh pattern will change with collapse or expansion of the overall structure, and may be selected to affirmatively limit the lower bounds of collapse diameter, as well as the upper bounds of expansion diameter.

FIG. 2C depicts another braiding assembly (18) wherein each of the braided fibers actually comprises a plurality of parallel fibers grouped together (22); the pattern of FIG. 2C has groups of approximately three small fibers travelling the woven, braided, or meshed pattern together.

U.S. Pat. Nos. 4,954,126; 4,655,771; 5,527,282; 5,061,275 and 5,221,261 disclose braided mesh configurations suitable for use in the present invention and are incorporated by reference herein in their entireties. These helical body configurations include a plurality of fibers each of which extends in a helix configuration along the center line of the helical body as a common axis, the fibers defining a radially self-expanding body, which comprises a first number of fibers having a common direction of winding but being axially displaced relative to each other and crossing a second number of fibers also axially displaced relative to each other but having an opposite direction of winding.

In one embodiment, the fibers may comprise a polymeric material such as polyester, polyamide, polypropylene, or copolymers thereof. In one embodiment the fibers each may have a cross sectional diameter of between about 0.003 inches and about 0.015 inches. In one embodiment the braiding, mesh, or weave pattern may produce pores in the expandable sheath wall material which have a diameter between about 0.002 inches and about 0.20 inches. In one embodiment a nonporous coating layer on the proximal portion of the expandable sheath assembly may comprise a flexible polymeric material such as silicone rubber, olefin block copolymers, and/or copolymers thereof.

Figure 2G:
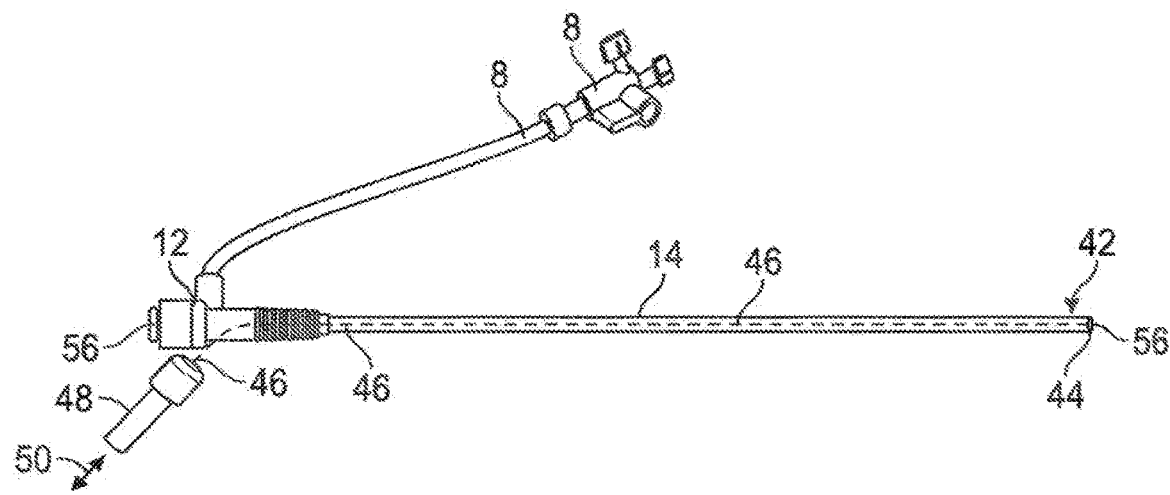

When the braided fiber assemblies such as assemblies (16, 18) are tensioned (i.e., from either end), they will decrease in overall geometry as the fibers comprising such assemblies move relative to each other; similarly, when such assemblies are compressed, they will increase in overall geometry. This factor may be controllably utilized to assist with delivery and use of the subject elongate instrument. For example, referring to FIG. 2G, in one embodiment, an elongate loading member (46), such as a pull-wire or push-wire (which may also be called a pushrod), may be operatively coupled between the distal end (42) of the introducer sheath tubing member (14), such as by direct mechanical coupling to a distal ring member (44) coupled to the distal tip (42) of the introducer sheath tubing member (14) and proximal coupling to a proximal control interface (48) such as a pull or push handle configured to allow an operator to manually apply tensile or compressive loads (50) to the elongate loading member (46). Such a coupling configuration allows for manually-actuated and controlled expansion or contraction of the introducer sheath tubing member (14) from a proximal location. Referring ahead to FIG. 2N, other associated structures, such as a dilator assembly or portions thereof, and/or a temporary locking member (80), may be utilized to place an introducer sheath tubing member (14) into a sustained tensile loading configuration (FIG. 2N illustrates an embodiment utilizing a locking member 80 to lock two portions of a dilator assembly (an inner dilator member 64 and an outer dilator member 66) into a loading configuration against each other, with the inner dilator member in tension and outer dilator member in compression, such that a distal portion of the sheath tubing member 14 remains intercoupled in between such dilator members 64, 66, and such that the introducer sheath tubing member 14 may be actively and sustainably pulled into tension to retain a decreased cross sectional diameter until the locking member 80 is removed) to assist with insertion or removal of the introducer sheath tubing member (14) relative to the associated anatomy.

Figure 2H:
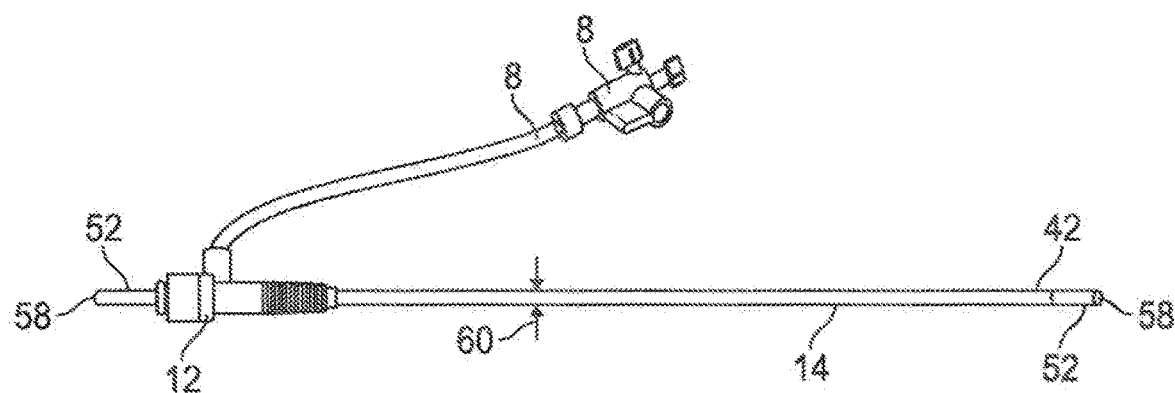
Figure 2I:
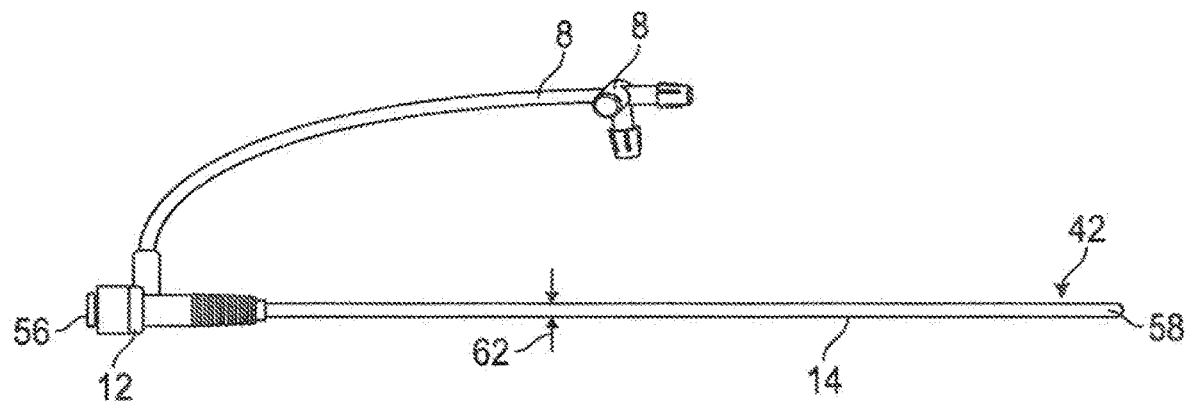

Referring to FIG. 2H, in another embodiment, it may be desirable to insert a tubular liner member (52), such as a polymeric tubular member, defining a tubular liner member lumen therethrough, to assist with insertion and/or withdrawal of structures through the introducer sheath tubing member (14). The tubular liner member may be selected to have a higher structural modulus than that of the introducer sheath tubing member (14) to effectively provide some rigidity and kink resistance to the overall assembly. The inner diameter of the tubular liner member (52) preferably will be sized to define a working lumen therethrough that will accommodate selected instrumentation without substantial expansion of the tubular liner member (52), and insertion of the tubular liner member (52) generally will urge the associated introducer sheath tubing member (14) from a relatively collapsed configuration to a relatively expanded configuration; removal of the tubular liner member will allow the introducer sheath tubing member (14) to return to the relatively collapsed configuration; this is demonstrated in the difference in outer diameters (60, 62) of the depicted introducer sheath tubing member (14) in FIG. 2H with the tubular liner member (52) in place urging the introducer sheath tubing member (14) to the more expanded configuration, and FIG. 2I with the tubular liner member removed, allowing the introducer sheath tubing member (14) to return to the relatively collapsed configuration.

Figure 2J:
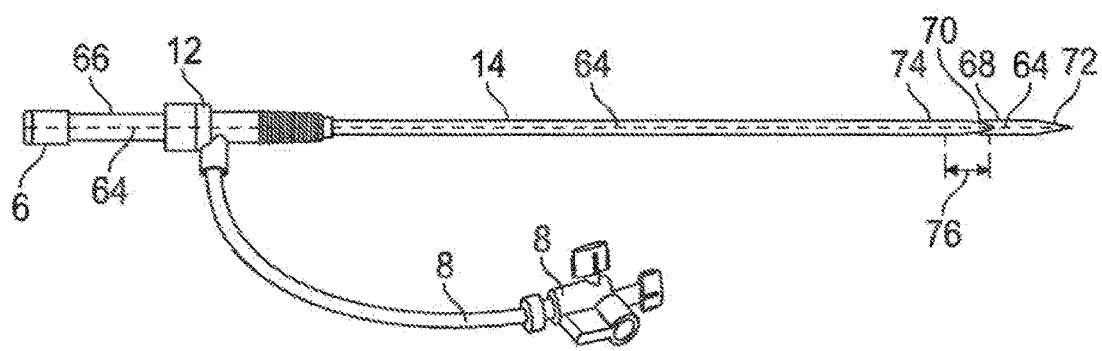

Referring to FIG. 2J, an assembly is shown utilizing an introducer sheath tubing member (14) along with other structures in a cardiovascular access configuration. In this embodiment, a two-part dilator assembly is used, as described above in reference to FIG. 2N. The assembly comprises an inner dilator assembly (comprised of an inner elongate dilator member 64 fixedly coupled to a distal dilator tip 68 having a tapered distal portion 72; the proximal portion of the inner elongate dilator member is fitted through the seal of the hub 12 and coupled proximally to a luer assembly 6) movably coupled to an outer elongate dilator member (66). This dilator assembly is fitted through the hub (12) and through the introducer sheath tubing member (14), with the exception of the tapered distal portion (74) of the introducer sheath tubing member (14), which is coupled into a tapered recessed inner geometry (70) of the proximal aspect of the dilator tip member (68) in a slightly compressed manner. As described above and further below in reference to FIG. 2N, with the distal portion of the sheath tubing member (14) intercoupled between the inverse taper (70) of the dilator tip member (68) and the tapered distal portion (78) of the outer dilator member (66), the sheath tubing member (14) may be tensioned to reduce cross sectional geometry by further inserting the outer dilator member (66) while the distal portion of the sheath tubing member (14) remains pinched and therefore coupled between the dilator tip member (68) and tapered end portion (78) of the outer dilator member (66); without this pinching constraint, the distal portion of the sheath tubing member (14) may be allowed to freely escape from the dilator tip member (68).

Figure 2K:
Figure 2L:
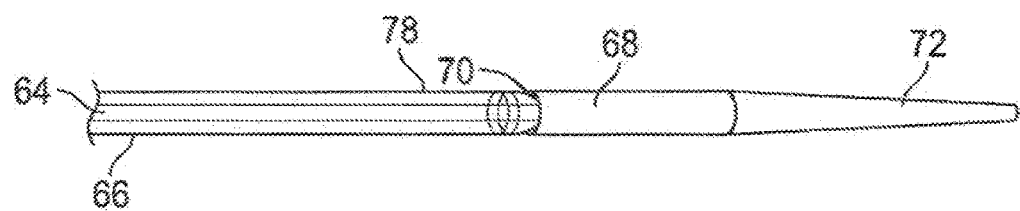
Figure 2M:
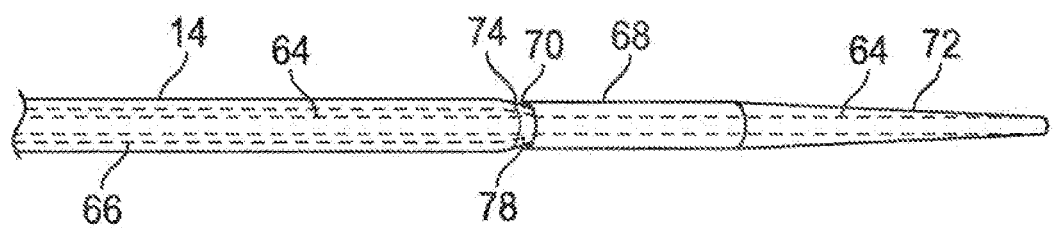
Figure 2N:
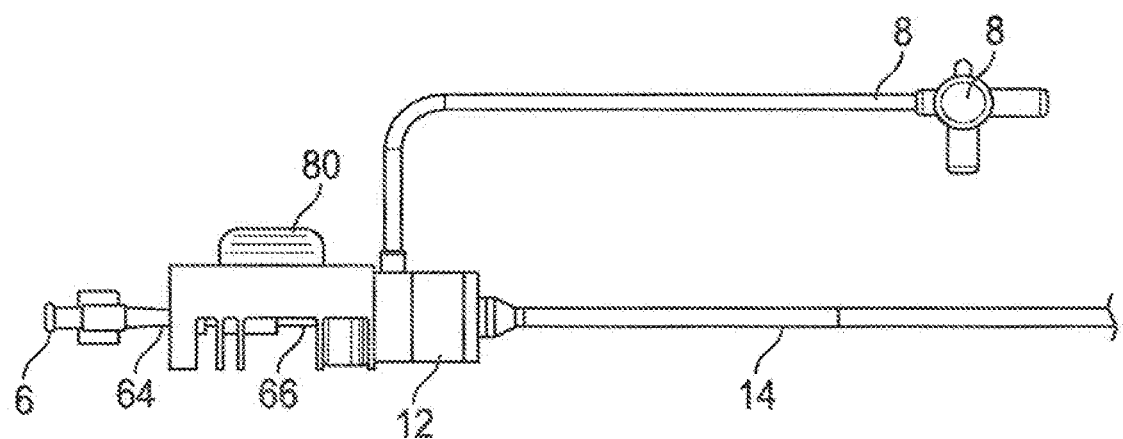

FIG. 2K illustrates an inner dilator assembly comprising an inner elongate dilator member (64) coupled to a dilator tip member (68) having a tapered distal portion (72) and a tapered proximal interior surface (70) for restrainably coupling with another tapered member which may be inserted into it, such as the distally tapered (78) outer dilator member (66) of FIG. 2L, or the distally tapered (74) introducer sheath tubing member (14) of FIG. 2M. FIG. 2M also illustrates that the outer dilator member (66—shown in dashed) may be inserted through the lumen of the introducer sheath tubing member (14) to capture a distal portion of the introducer sheath tubing member (14) in a pinched coupling manner between the outer dilator member (66) and the dilator tip member (68) which is coupled to the inner dilator member (64—also dashed), as described in reference to FIG. 2N.

As described above, FIG. 2N illustrates that a locking member (80) may be temporarily positioned between the hub (12) and a proximal portion of a dilator member (64) to place an introducer sheath tubing member (14) in tension between the hub (12) and dilator tip (68) to reduce the overall cross-sectional geometry of the introducer sheath tubing member (14) for improved insertion/withdrawal performance.

Figure 2O:
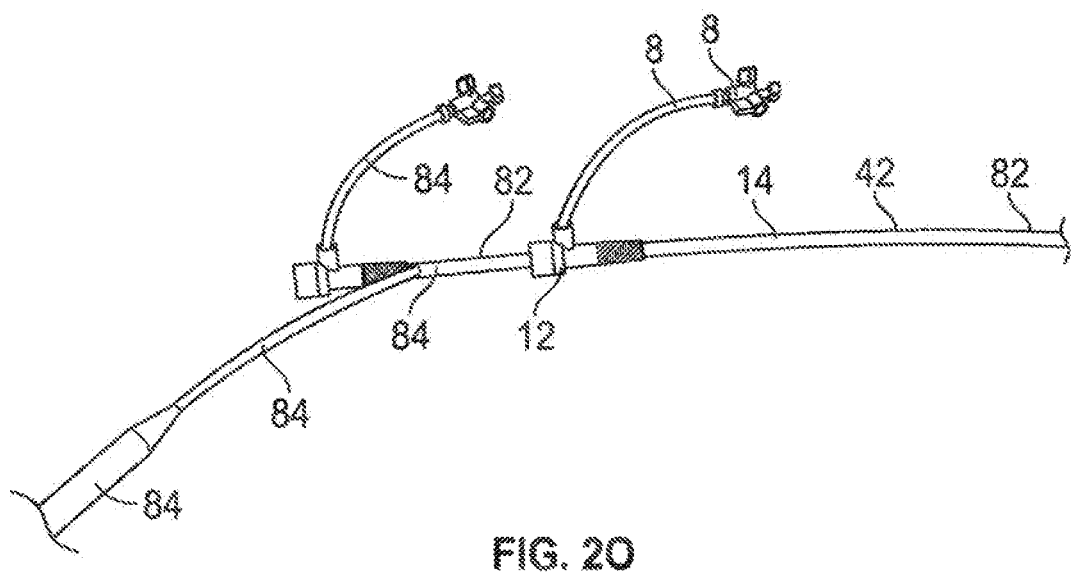

Referring to FIG. 2O, an interventional assembly (84), such as variations described in U.S. Patent Application Ser. No. 61/822,204, incorporated by reference herein in its entirety, the assembly (84) comprising an elongate tubular member (82), may be utilized with an introducer sheath tubing member (14) as described herein.

Referring to FIGS. 3-12, various configurations for procedures utilizing an expandable introducer sheath such as those described above are illustrated.

Figure 3:
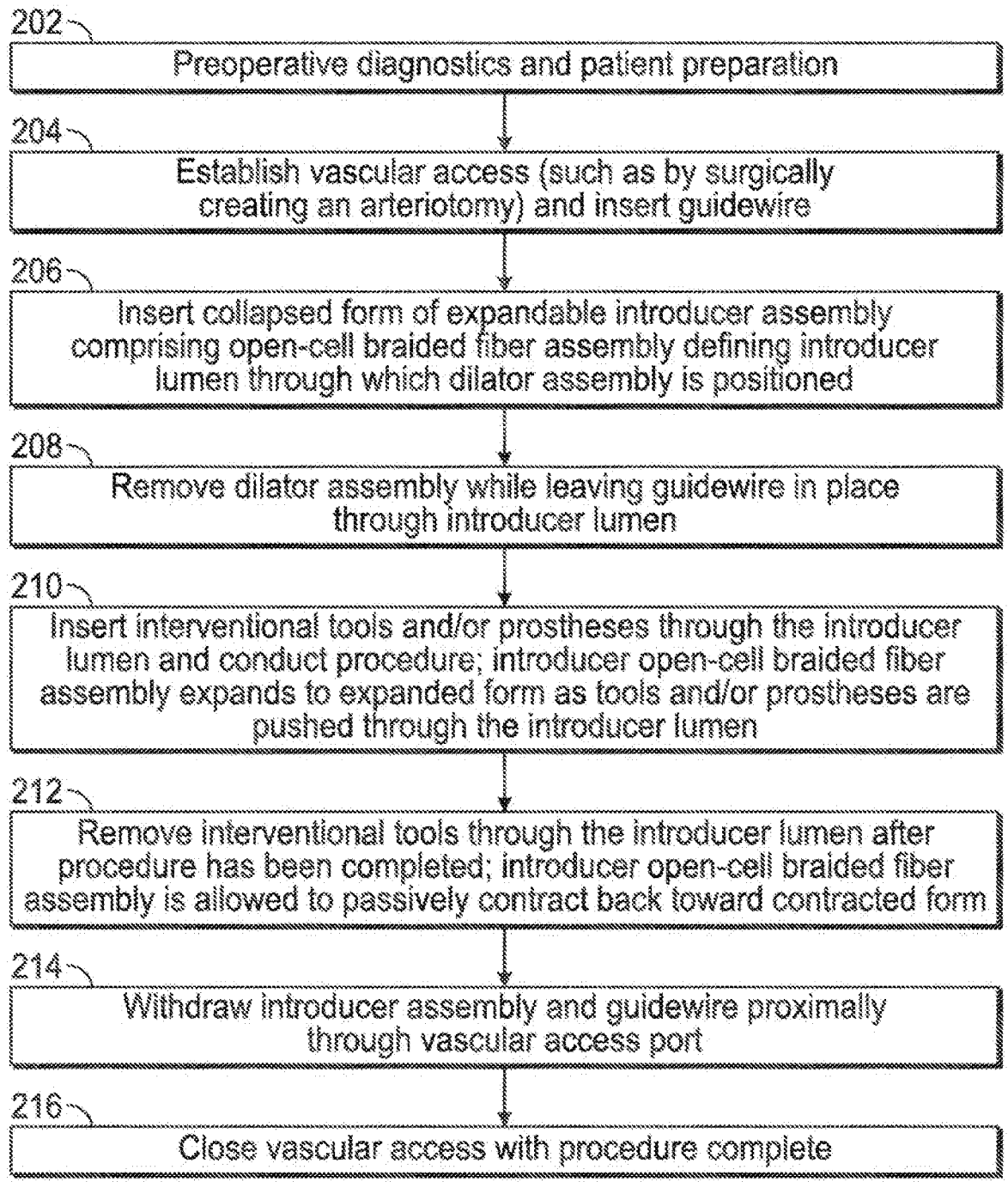
FIG. 3 illustrates various aspects of a minimally invasive access technique in accordance with the present invention.

Referring to FIG. 3, after preoperative diagnostics and patient preparation (202), vascular access may be established, such as by a surgically-created arteriotomy cut-down, and a guidewire may be inserted (204), such as an 0.035" diameter guidewire. A collapsed form (i.e., with a first inner lumen diameter of between about 0 mm and about 4 mm) of an expandable introducer assembly comprising an open-cell braided fiber tube or tubular assembly may be inserted (206). In one embodiment the expandable fiber assembly may be expanded to provide inner working lumen diameters of between about 4 mm and about 7 mm, for example. With the tubular introducer sheath assembly in place, the associated dilator assembly may be removed (208). In one embodiment this may be accomplished by advancing the distal portion of the dilator assembly relative to the intercoupled braided expandable sheath to release the distal end of the expandable sheath from tension between the dilator distal portion and the hub (as described above in reference to FIG. 2N), allowing it to expand to provide an inner diameter sufficient to allow the dilator distal portion to be proximally withdrawn through the working lumen I inner diameter of the expandable sheath. At such point, the expandable sheath is in place relatively unconstrained, and the guidewire remains in place through the working lumen of the expandable sheath. In one embodiment one or more radio-opaque markers may be coupled to the expandable sheath assembly to assist with imaging confirmation of deployment location. Referring again to FIG. 3, interventional and/or diagnostic tools and/or prostheses may be inserted through the expandable sheath, thereby further expanding the sheath (210). Expansion of the expandable sheath may be localized, such that after a relatively large member is passed through and past a given portion of the sheath, that portion re-collapses, at least partially. After utilization of the interventional and/or diagnostic tools has been completed, they may be withdrawn proximally until there are removed, and the expandable sheath may be allowed to further collapse or contract in diameter (212). Subsequently the collapsed expandable sheath and guidewire may be proximally withdrawn (214) and the surgical access closed (216).

Figure 4:
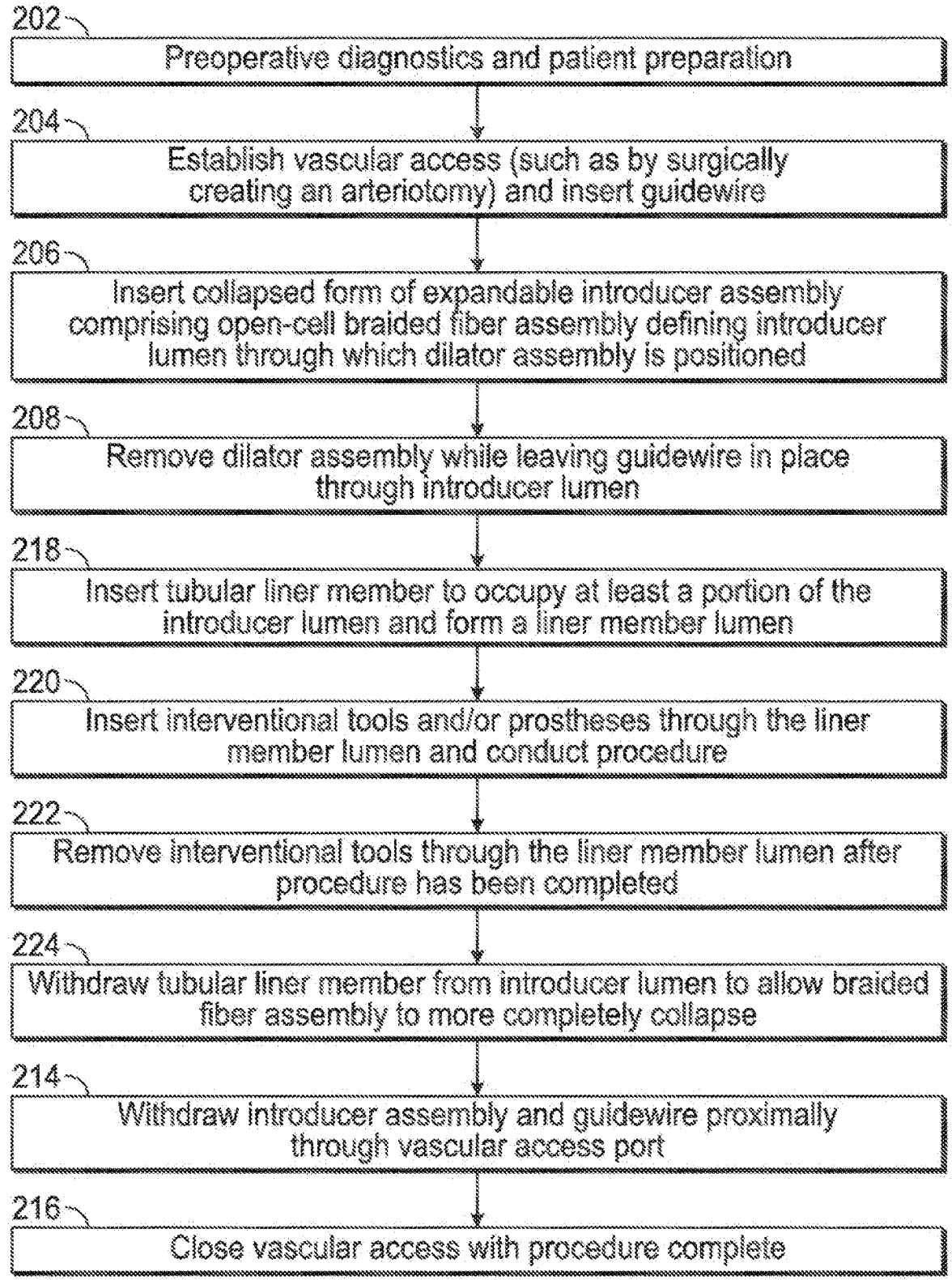
FIG. 4 illustrates various aspects of a minimally invasive access technique in accordance with the present invention.

Referring to FIG. 4, an embodiment similar to that of FIG. 3 is depicted, with the exception that steps 210 and 212 of the embodiment of FIG. 3 have been replaced with steps 218, 220, 222, and 224, wherein a tubular liner is inserted to occupy at least a portion of the expandable introducer lumen, and to form a lumen within the liner which may be utilized as the new working lumen (218); tools for interventional and/or diagnostic procedure steps may be inserted through the liner lumen while the procedure is conducted (220); after the procedure has been completed the tools may be withdrawn out through the liner lumen (222), and subsequently the tubular liner itself may be withdrawn (224) to allow the expandable sheath to form a more collapsed geometry for withdrawal of such expandable sheath (214).

Figure 5:
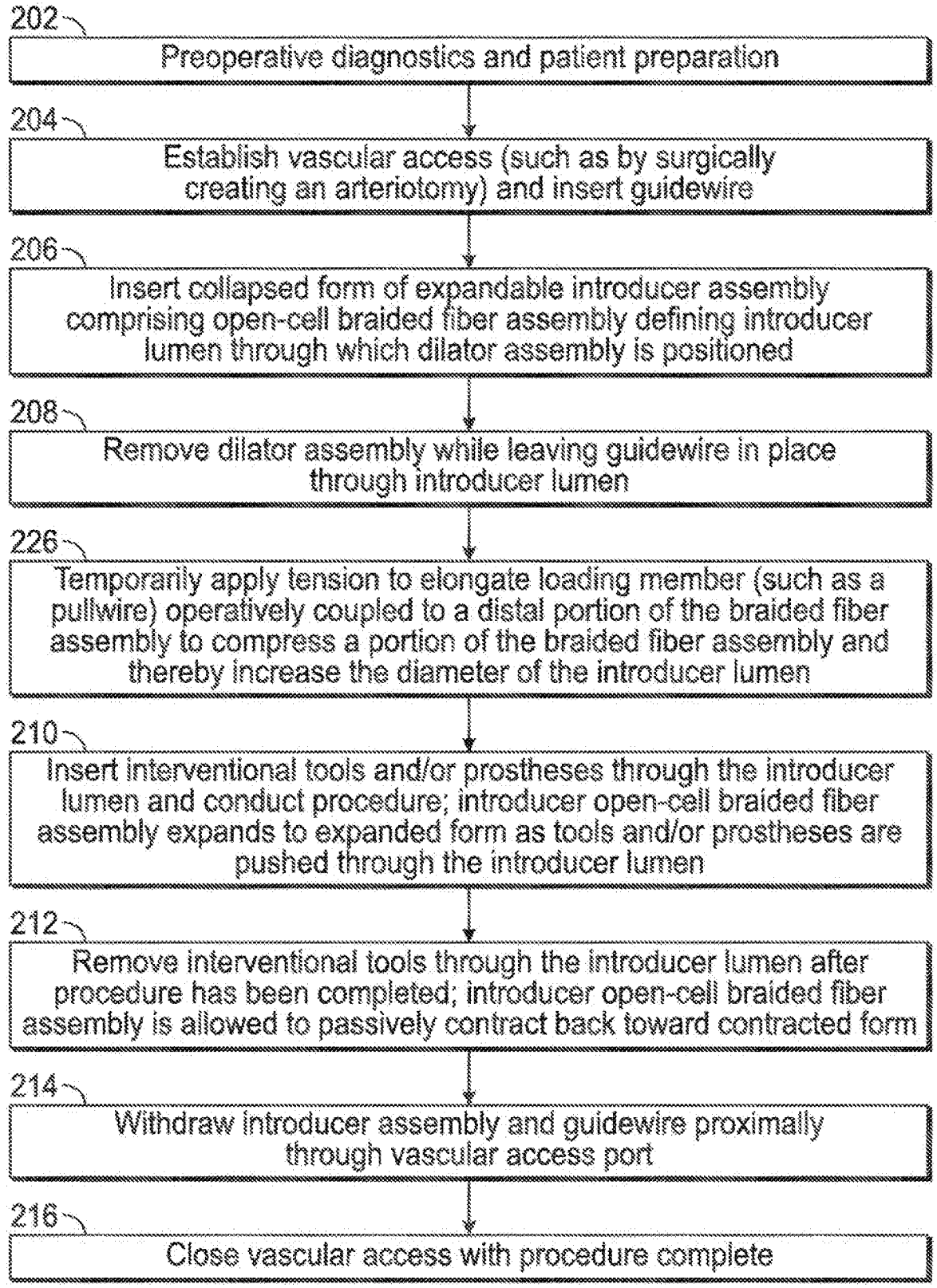
FIG. 5 illustrates various aspects of a minimally invasive surgical access technique in accordance with the present invention.

FIG. 5 illustrates an embodiment similar to that of FIG. 3, with the exception that an additional step is included (226) wherein an elongate loading member may be tensioned to place the braided fibrous expandable sheath into compression, thereby forcibly increasing the diameter of the associated defined introducer lumen for easier passage of structures through such introducer lumen.

Figure 6:
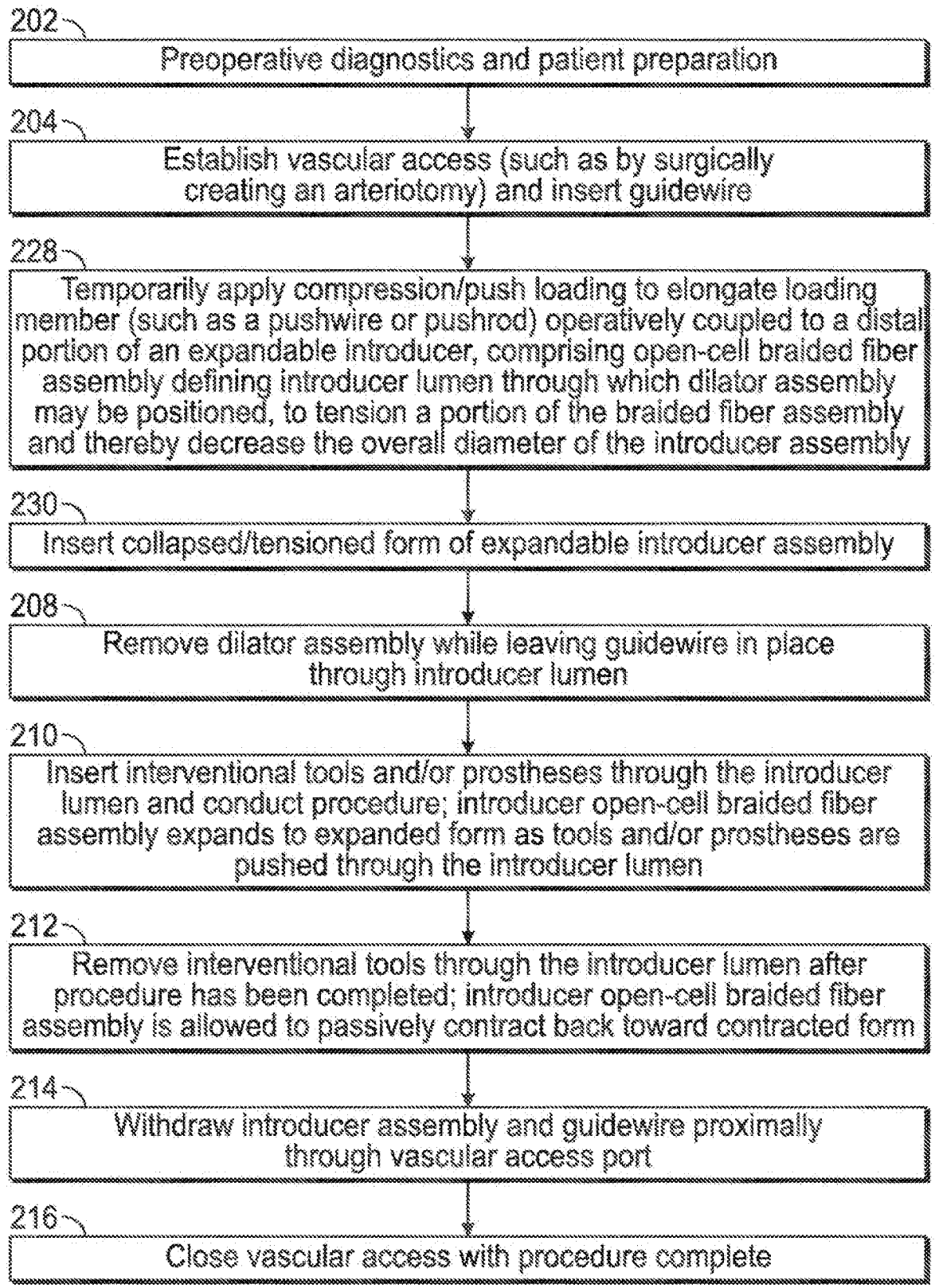
FIG. 6 illustrates various aspects of a minimally invasive surgical access technique in accordance with the present invention.

FIG. 6 illustrates an embodiment similar to that of FIG. 3, with the exception that insertion of the expandable sheath assembly is facilitated by forcibly minimizing the diametric geometry of the expandable sheath using a push-wire to create tensile loading of the expandable sheath during insertion (228, 230).

Figure 7:
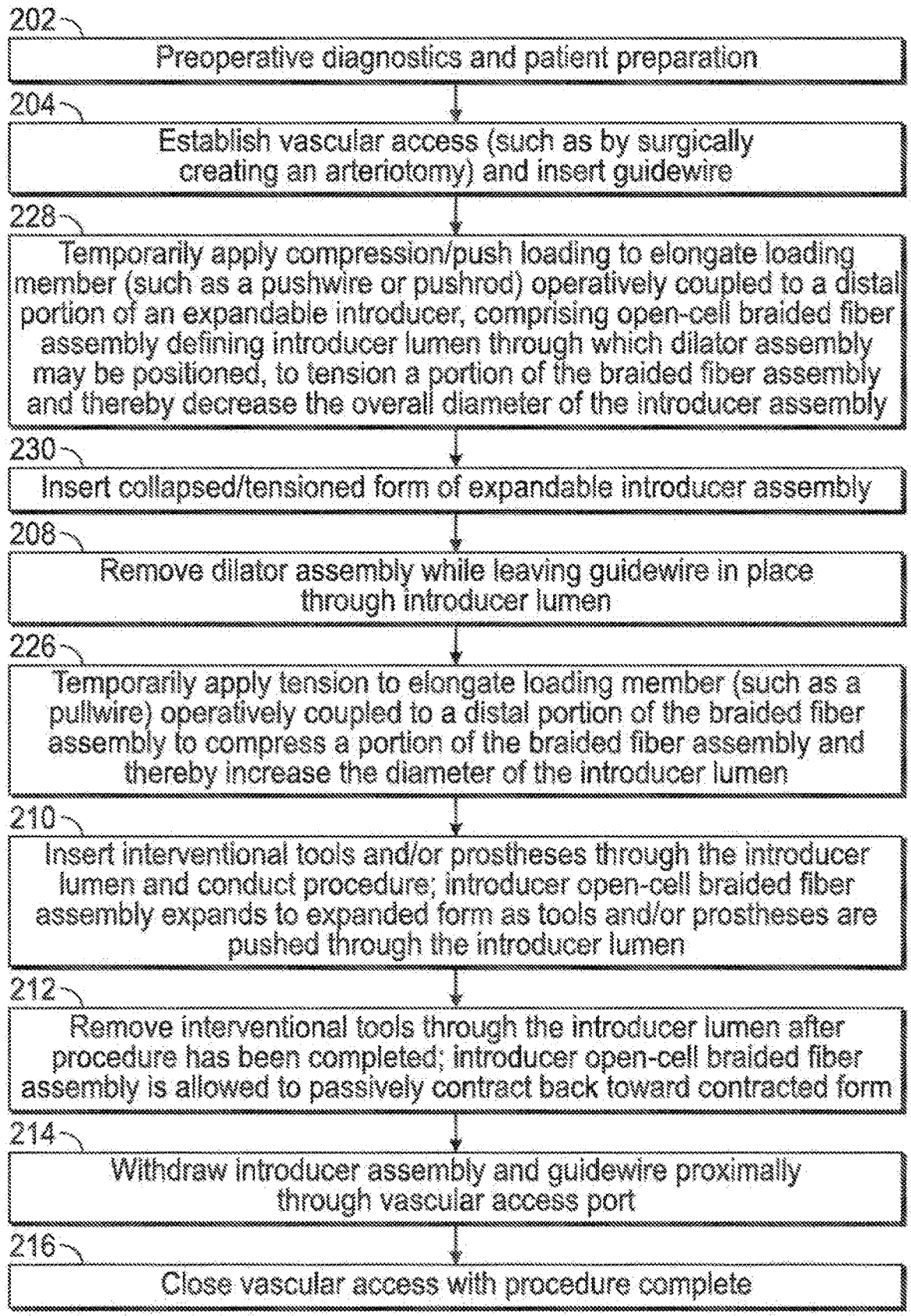
FIG. 7 illustrates various aspects of a minimally invasive surgical access technique in accordance with the present invention.

FIG. 7 combines the differences of the embodiments of FIGS. 5 and 6 relative to that of FIG. 3, both in the same embodiment/procedure, such that tension is controllably applied to minimize the outer geometry of the expandable sheath member during insertion (228, 230), and such that compression is controllably applied to maximize the geometry of the expandable sheath member for insertion of instrumentation therethrough (226)

Figure 8:
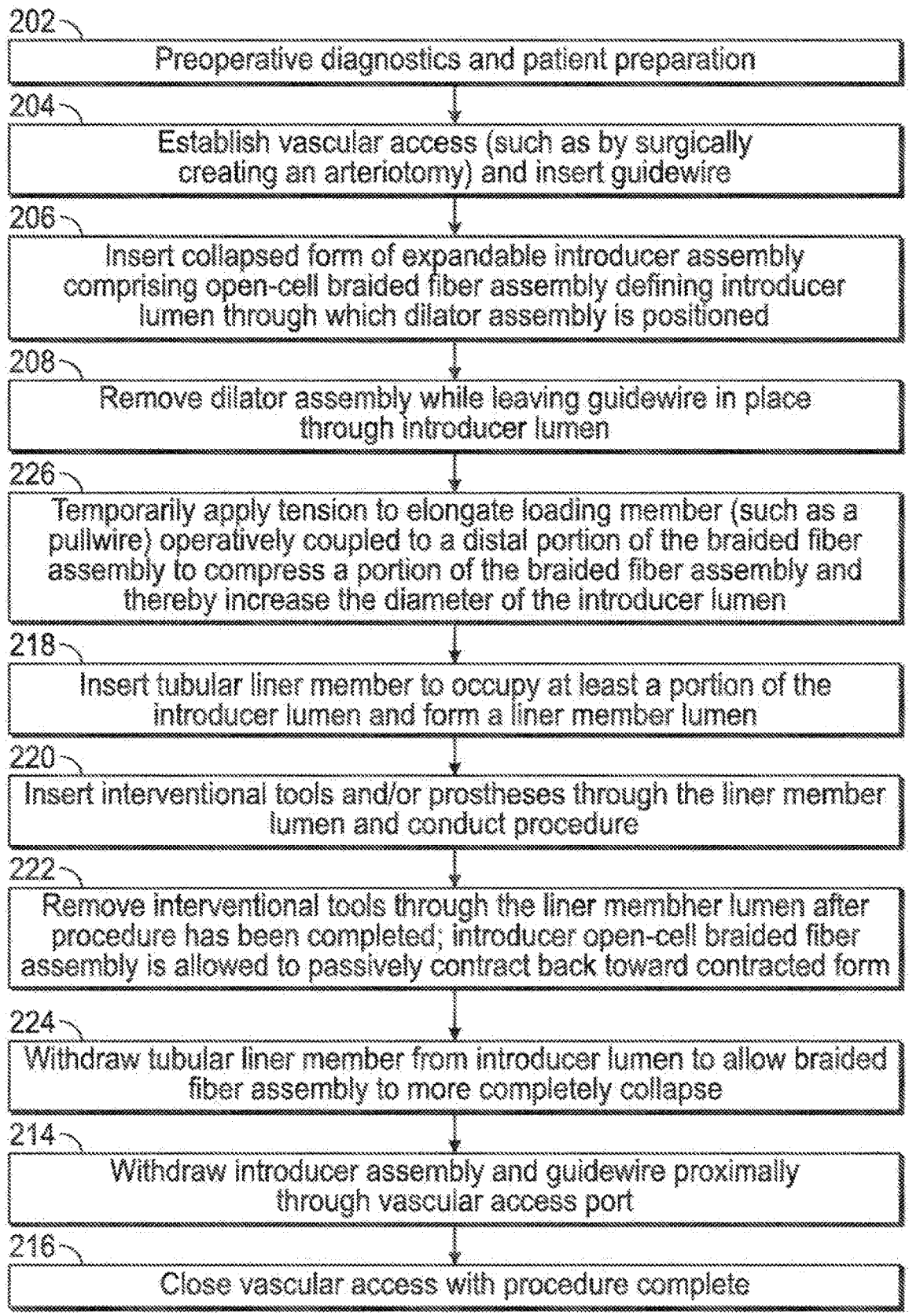
FIG. 8 illustrates various aspects of a minimally invasive surgical access technique in accordance with the present invention.

FIG. 8 illustrates an embodiment similar to that of FIG. 4 wherein a tubular member or liner may be inserted into the expandable sheath to assist with sheath expansion and insertability I retractability of instrumentation (218, 220, 222, 224); also combined into this embodiment is the aforementioned aspect of creating compressive loading of the expandable sheath member to maximize the geometry of the expandable sheath member for insertion of instrumentation therethrough (226).

FIG. 9 illustrates an embodiment similar to that of FIG. 4 wherein a tubular member or liner may be inserted into the expandable sheath to assist with sheath expansion and insertability I retractability of instrumentation (218, 220, 222, 224); also combined into this embodiment is the aforementioned aspect of creating tensile loading of the expandable sheath member to minimize the geometry of the expandable sheath member for insertion or withdrawal from the vasculature (228, 230).

Figure 10:
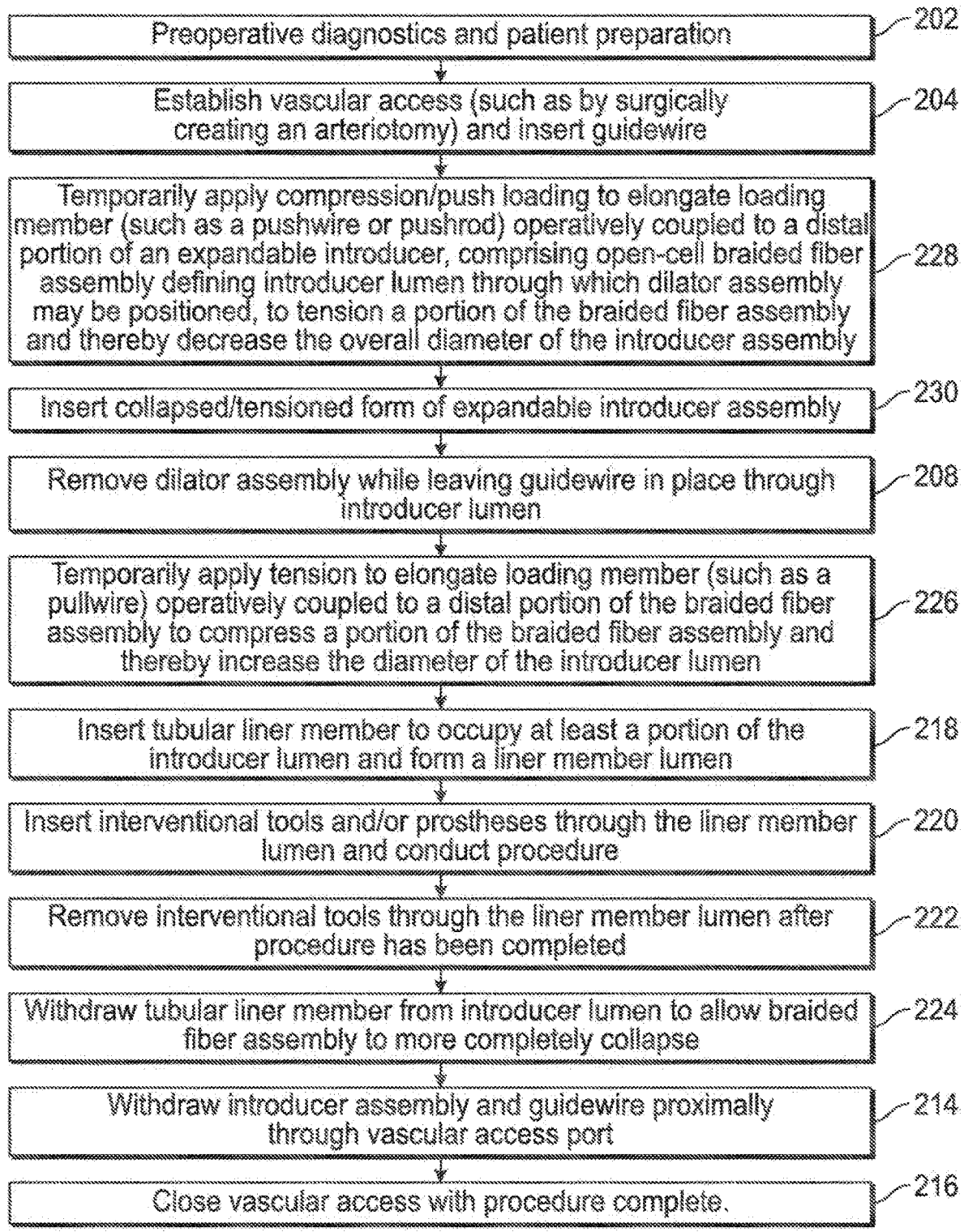
FIG. 10 illustrates various aspects of a minimally invasive surgical access technique in accordance with the present invention.

FIG. 10 illustrates an embodiment similar to that of FIG. 4 wherein a tubular member or liner may be inserted into the expandable sheath to assist with sheath expansion and insertability I retractability of instrumentation (218, 220, 222, 224); also combined into this embodiment is the aforementioned aspect of creating compressive loading of the expandable sheath member to maximize the geometry of the expandable sheath member for insertion of instrumentation therethrough (226), as well as the aforementioned aspect of creating tensile loading of the expandable sheath member to minimize the geometry of the expandable sheath member for insertion or withdrawal from the vasculature (228, 230).

FIG. 11 illustrates an embodiment similar to that of FIG. 7, with additional emphasis on having a dilator assembly comprising two or more parts (232), such as that shown in FIG. 2J.

Figure 12:
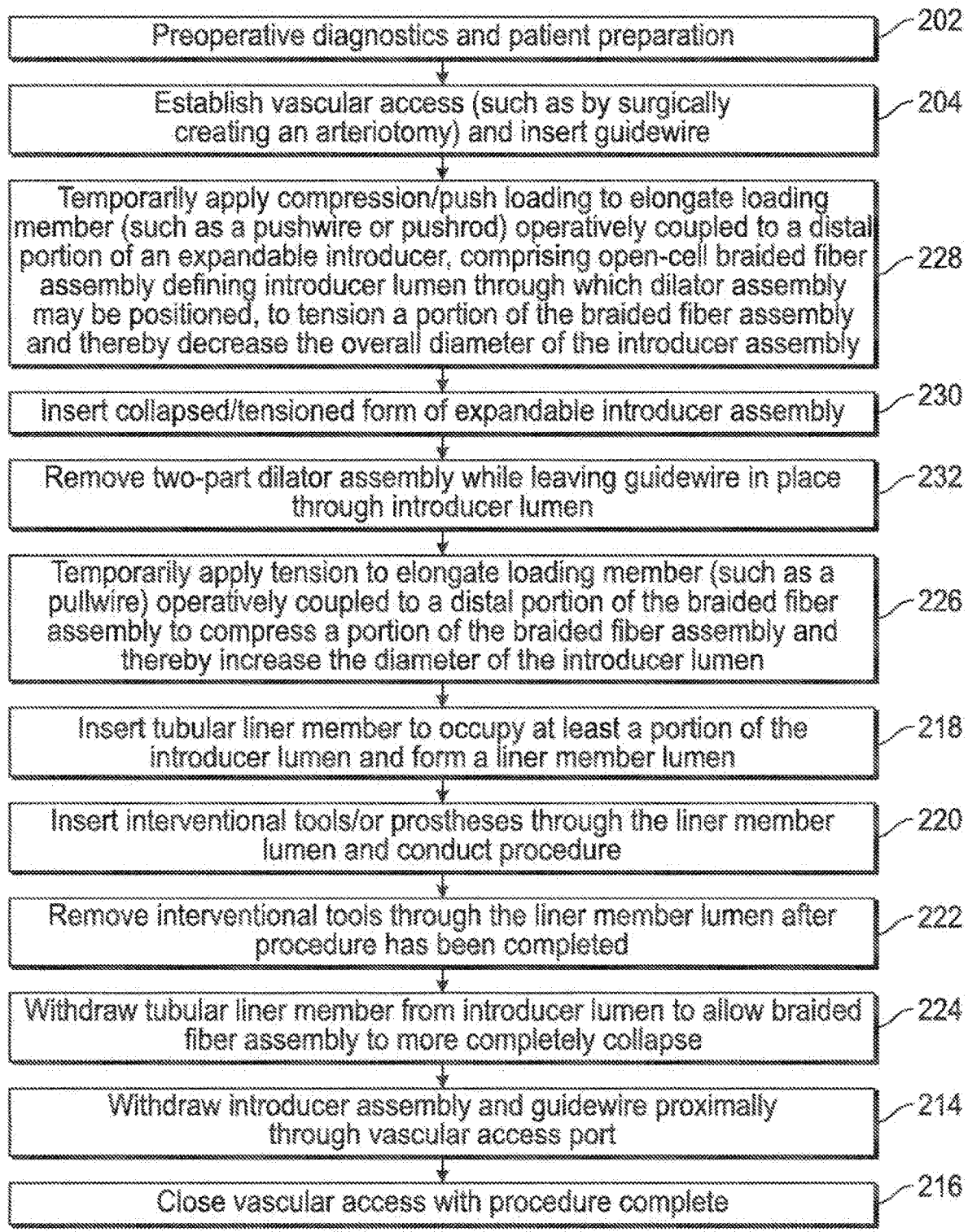
FIG. 12 illustrates various aspects of a minimally invasive surgical access technique in accordance with the present invention.

Similarly, FIG. 12 illustrates an embodiment similar to that of FIG. 10, with additional emphasis on having a dilator assembly comprising two or more parts (232), such as that shown in FIG. 2J.

FIG. 13 illustrates an exploded view 300 of another embodiment of an introducer sheath assembly, a dilator assembly, and a clip in which the introducer sheath assembly 301 is provided with a proximal section 303 which is more rigid than distal flex section 304. The dilator assembly 305 comprises dilator shaft 306, dilator sheath 307 and dilator tip 308 along with clip 309. As described below, when assembled, the elements of FIG. 13 are arranged in the same general manner as illustrated in FIGS. 2J-2N.

Figure 14A:
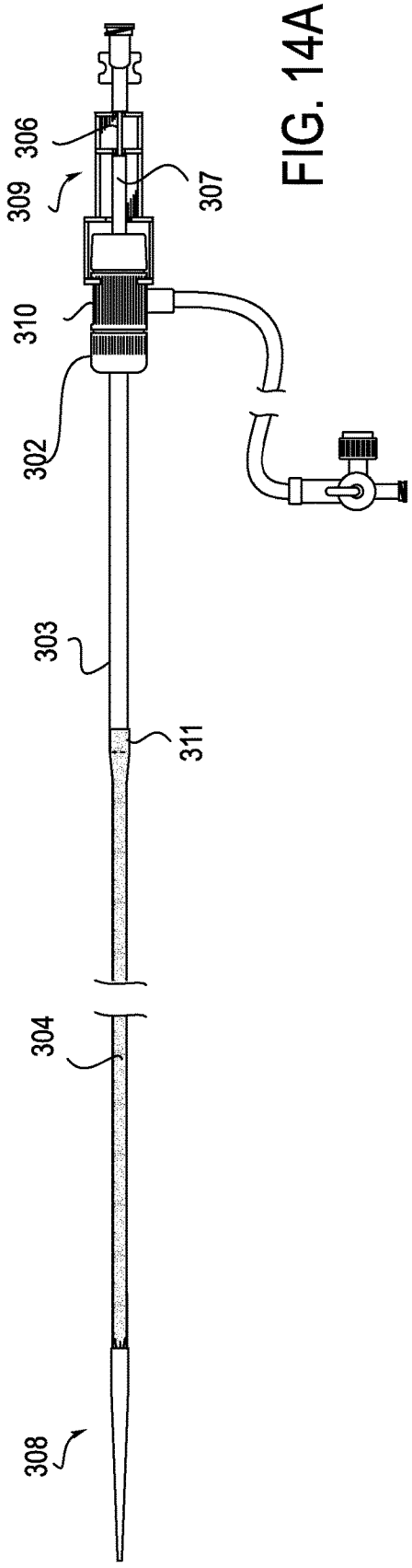
FIGS. 14A and 14B illustrate the embodiment of FIG. 13 in assembled form.
Figure 14B:
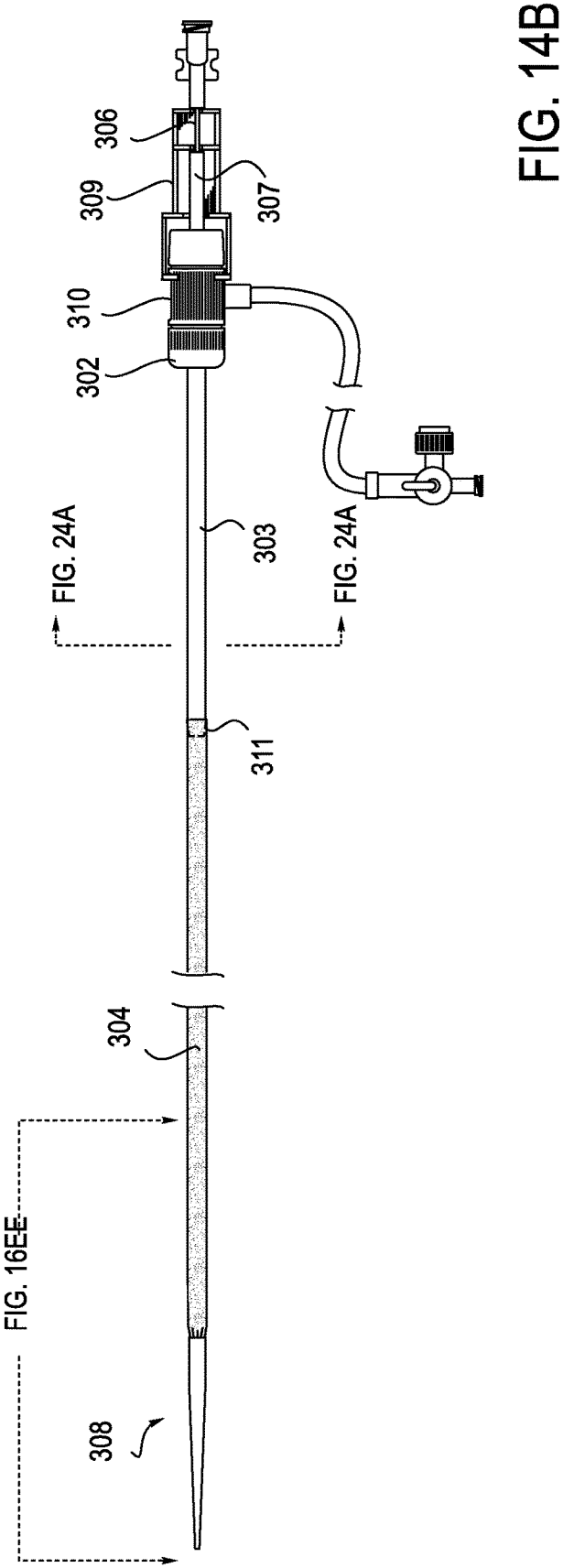

FIGS. 14A and 14B illustrate the introducer sheath assembly, dilator assembly and clip of FIG. 13 in assembled form. As shown in these figures, the dilator shaft and dilator sheath of dilator assembly 305 extend through a lumen in introducer sheath 301 and terminate in dilator tip 308 which extends distally from distal flex section 304 of introducer sheath 301. FIG. 14A also shows the location of clip 309 in relation to hub 302 and clip lock recess 310 in hub 302. The fixation region 311 of the mesh of distal flex section 304 to proximal section 303 is also shown. FIG. 14B shows the location of the transverse cross-section shown in FIG. 24A and FIG. 14B shows the location of the longitudinal cross-section shown in FIG. 16E.

FIG. 15A shows dilator assembly 305 in an exploded view with dilator sheath 307 shown separately from dilator shaft 306 and dilator tip 308. When assembled, dilator shaft 306 passes through the lumen 313 in dilator sheath 307 and the proximal end of dilator shaft 306 is provided with a luer lock 312. FIG. 15B shows the dilator assembly in assembled form and shows the location of the longitudinal cross-section shown in FIG. 16A. FIG. 15A also shows the external proximal bevel 314 and the external distal bevel 315 proximal portion 303 and the distal portion 304, respectively, of dilator sheath 307.

Figure 16A:
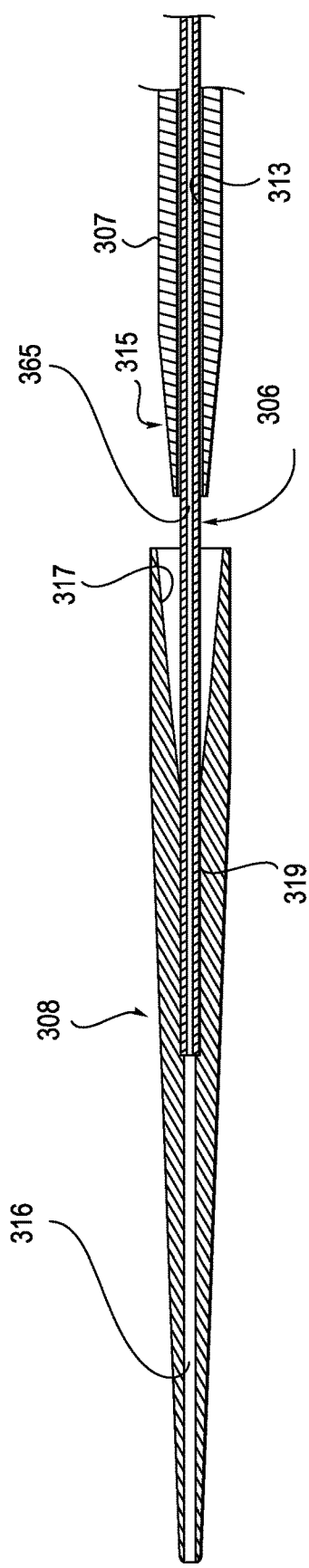
FIGS. 16A, 16B, 16C, 16D, 16E, and 16F illustrate the structure of the dilator tip, dilator shaft, and dilator sheath of the device of FIG. 13.

FIG. 16A shows the longitudinal cross-section of the distal region of the dilator assembly according the section line shown in FIG. 15B. As shown in FIG. 16A, the dilator shaft 306 extends into the proximal region of dilator tip 308 and is affixed to tip 308 in an intermediate region 319 of tip 308. As further shown in FIG. 16A, lumen 316 in the dilator tip is a continuation of lumen 365 in the dilator shaft. Dilator tip 308 is also provided with an internal bevel in its proximal region which has a shape which is complementary to that of external distal bevel 315 on dilator sheath 307.

Figure 16B:
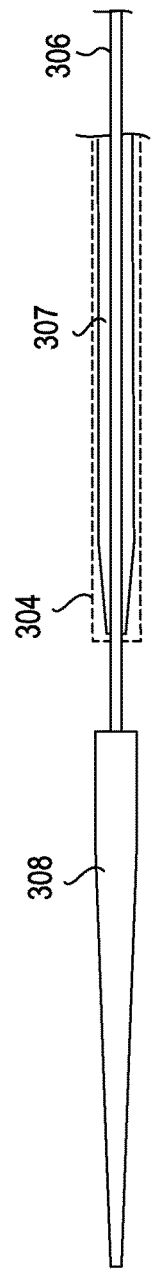
Figure 16C:
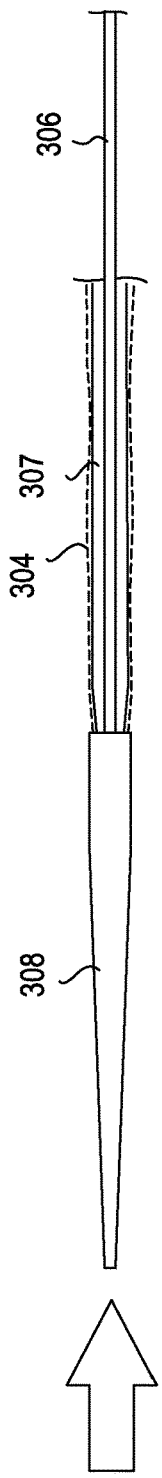
Figure 16D:
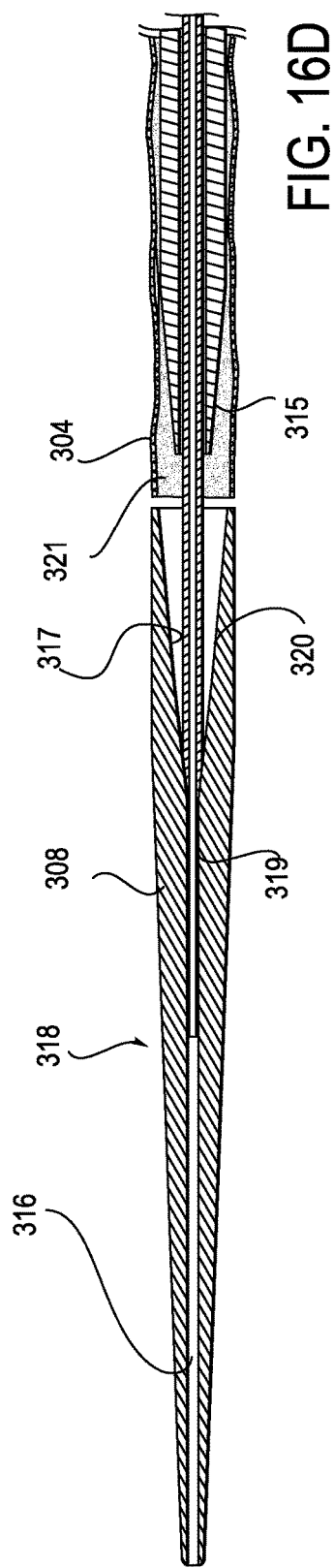
Figure 16E:
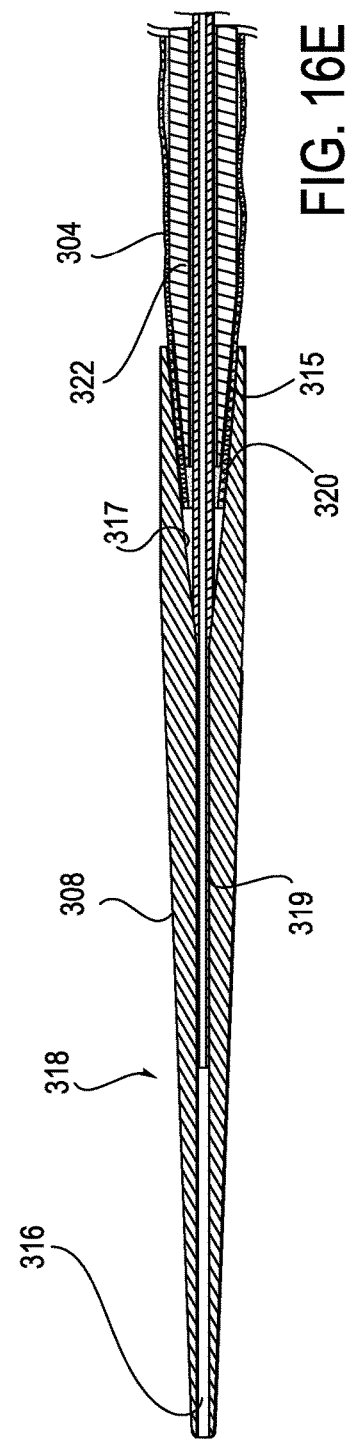
Figure 16F:
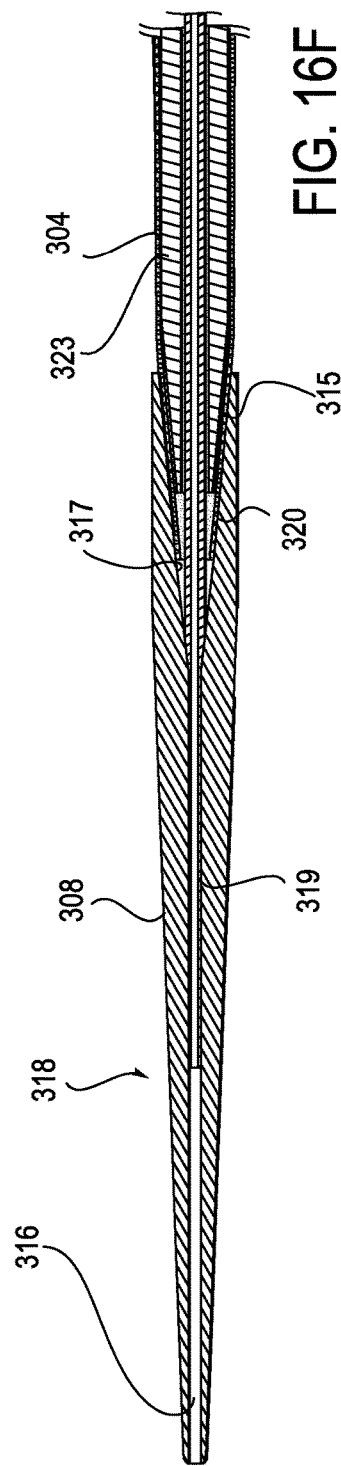

FIG. 16B illustrates the relationship of the dilator sheath 307 and the distal flex section 304 with dilator tip 308 before the dilator sheath and distal flex section are advanced into the dilator tip 308. FIG. 16C shows these elements after the dilator sheath and distal flex section have been advanced into the dilator tip. FIGS. 16D-F show this relationship in a series of cross-sectional views. In FIG. 16D, as in FIG. 16B, the dilator sheath and the distal flex section have not yet been advanced into mesh entrapment region 320 and the distal flex mesh is in a free state 321. In FIG. 16E, as in FIG. 16C, the dilator sheath 307 and the distal flex mesh 304 have been advanced into mesh entrapment region 320 such that the mesh is gripped by the beveled internal wall 317 of the dilator tip and the beveled external distal wall 315 of the dilator sheath such that the mesh is in the captured state 322. FIG. 16F shows the same elements after the mesh has been placed under tension and is in tensioned state 323.

FIG. 17 illustrates sheath 301 and shows an exemplary location for a radiopaque element 325 which can be provided to improve visibility under fluoroscopy or other similar techniques. FIG. 17 also shows the location of hemostatic valve 324 which, as indicated, is illustrated in more detail in FIGS. 31A-D.

FIGS. 18A-E show various mesh configurations with radiopaque marker 326 illustrated in FIG. 18A and radiopaque ring 327 illustrated in FIG. 18C. FIG. 18F shows radiopaque strand 328. A platinum or other radiopaque material could be used for strand 328. Alternatively, polymer strands in the mesh could be filled with a radiopaque material such as barium sulfate.

Figure 19C:
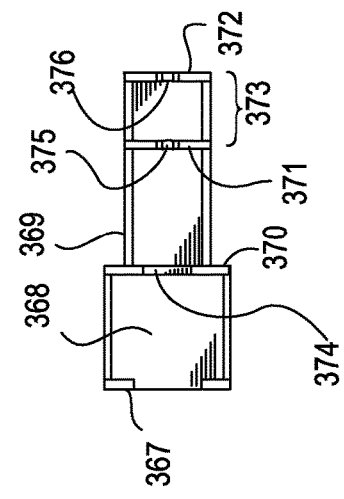
FIGS. 19A, 19A, 19B, 19C, 19D, 19E and 19F illustrate the clip which may be used in combination with the sheath assembly.
Figure 19A:
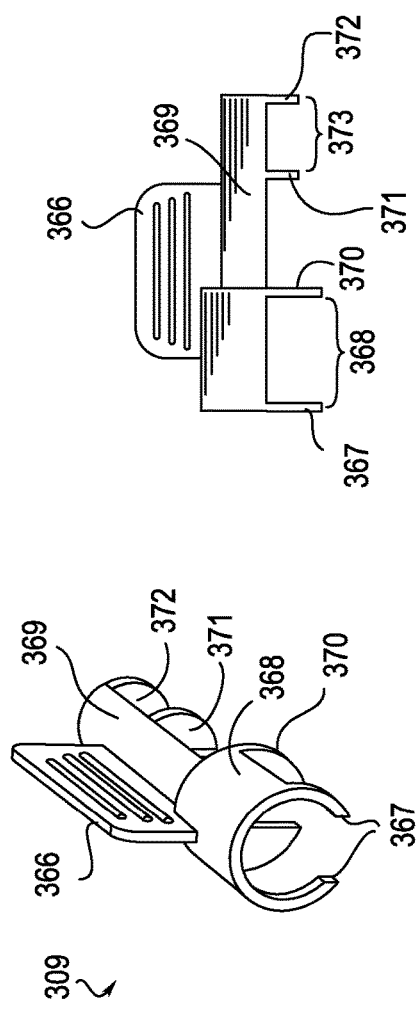
Figure 19B:
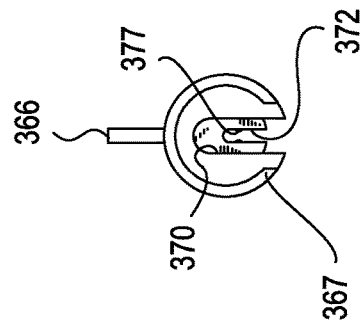
Figure 19D:
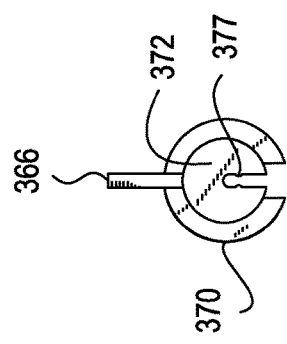
Figure 19F:
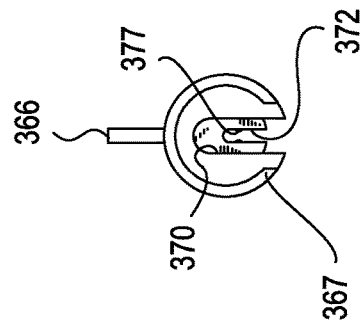
Figure 19E:
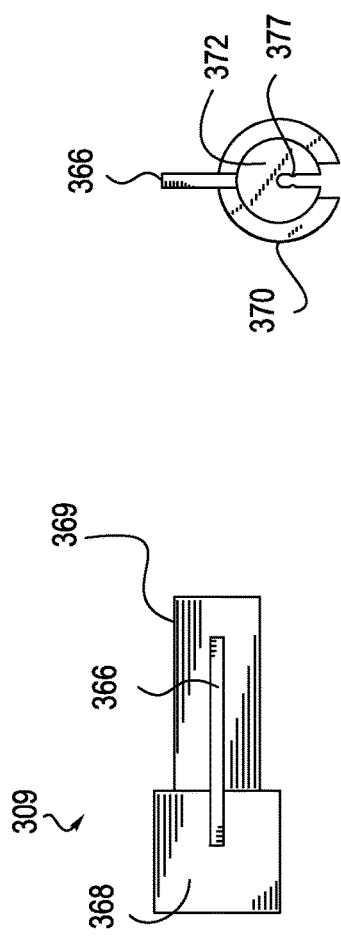

FIGS. 19A-F illustrate clip 309 in greater detail. FIG. 19A is a perspective view of clip 309 and shows handle 366, hub lock 367, hub engaging portion 368 and dilator housing compartment 369. FIGS. 19B-19F illustrate the clip as viewed from various vantage points. FIG. 19B is a side view, FIG. 19C is a bottom view, FIG. 19D is a top view, FIG. 19E is an end view as seen from the dilator engaging end and FIG. 19F is an end view as seen from the hub engaging end. In addition, FIG. 19B illustrates partition element 370 which separates the hub engaging portion of clip 309 from the dilator engaging portion 369. Also shown are the dilator sheath restraint 371 and the luer lock restraint 372 which define sheath tensioning section 373. Luer lock restraint 372 prevents distal displacement of the dialator shaft when the dilator shaft slides distally until the luer lock 312 abuts luer lock restraint 372.

FIG. 19C illustrates slot 374 in element 370 through which the dilator assembly passes, slot 375 in dilator sheath restraint 371 and slot 376 in luer lock restraint 372. FIG. 19D is a top view of clip 309. FIG. 19E illustrates lock nub 377 which constrains removal of the dilator shaft from slot 376 when the device is assembled, but which permits removal of the dilator shaft when sufficient force is applied, as seen from the dilator engaging end of the clip. FIG. 19F illustrates the same elements as seen from the hub engaging end of the clip.

The clip 309 is used to maintain the axial relationship of the introducer sheath, dilator sheath and dilator shaft as shown in FIGS. 14A and 14B. The clip tension sheath section 373 maintains the relationship between the distal bevel 315 of the dilator sheath and the proximal bevel 317 of the dilator tip. Section 368 of the clip 309 maintains the relationship between the introducer sheath 301 and the dilator assembly 305 which is adapted to place the sheath under tension which decreases the diameter of the distal flex section 304.

FIGS. 20A and 20B show, respectively, the distal flex mesh section 304 in the distal captured state 322 when not under tension and the distal flex section under tension by reason of actuation of clip 309. As shown in FIG. 20A when clip 309 is not installed over hub 302, distal mesh section 304 is not under tension and is slack. The diameter of distal flex section 304 can very according to the design of the mesh. For example, the diameter of the mesh in its relaxed state could be the same or similar to its diameter in the tensioned state. Furthermore, the diameter of the mesh in its relaxed state could be significantly larger in diameter than in the tensioned state such that, when tension is released, the mesh will self-expand. As further shown in FIG. 20A, dilator shaft is free to slide axially in dilator sheath 307 until the luer lock abuts the dilator sheath. When clip 309 is installed over hub 302 as shown in FIG. 20B, dilator sheath 307 is no longer free to slide within hub 302, but rather is locked in place by dilator sheath restraint 371 against which it abuts. However, dilator shaft 306 remains free to slide within dilator sheath 307 and is held in a proximally displaced location by luer lock restraint 372 which places mesh 304 under tension and reduces its diameter. Conversely, when clip 309 is removed from the sheath 301, the dilator shaft is free to move distally and may be advanced in a distal direction until the dilator tip 308 separates from the dilator sheath 307 to free the distal portion 304 of the sheath. When this is done, the dilator shaft 306 and dilator tip 308 together with dilator sheath 307 may be withdrawn from the introducer sheath. With introducer sheath 301 now being free of the dilator assembly, a device to be deployed may be passed through the introducer sheath and delivered to a desired location.

Figure 21:
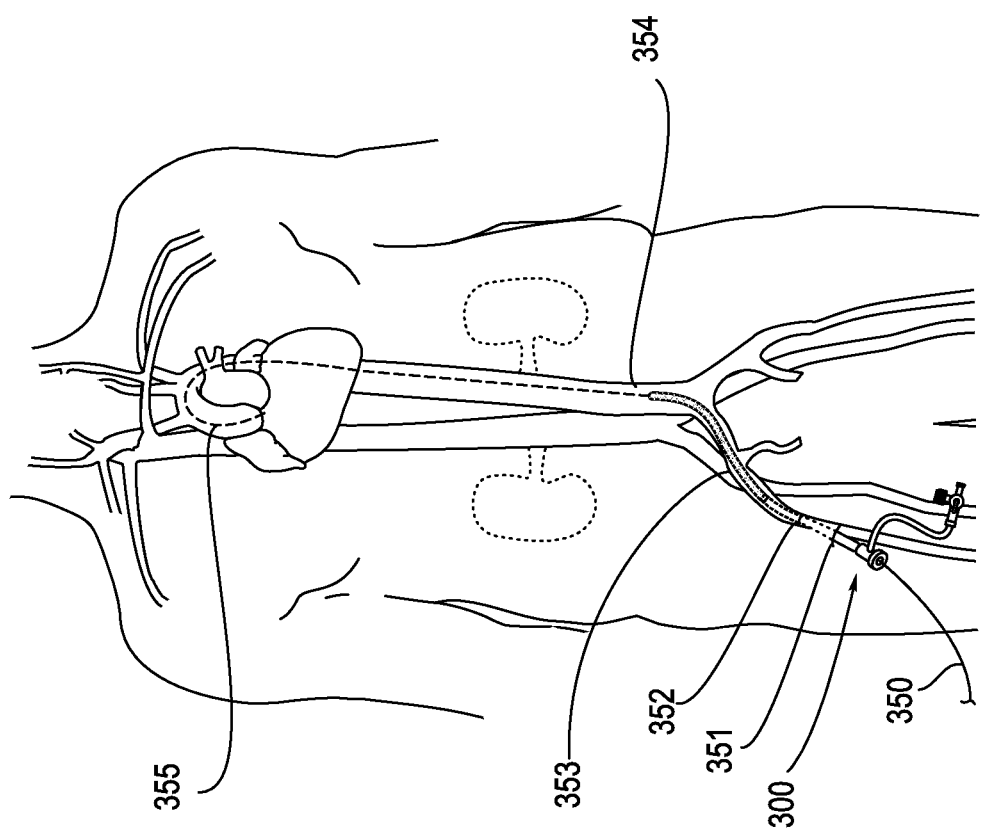
FIG. 21 illustrates the relevant anatomy with the sheath assembly deployed in the vasculature.

FIG. 21 illustrates the anatomy relevant to the present invention with a diagrammatic view showing an embodiment installed in a patient. As shown, an expandable introducer 300 is introduced over guidewire 350 and enters the body at femoral artery access point 351 and enters the artery at vessel puncture site 352. Guidewire 350 has previously been deployed through the femoral artery, the right common iliac 353 and through aorta 354 until it reaches the ascending aorta as shown by the dotted line. As shown in FIG. 21, the expandable introducer is introduced into the right common iliac 353 and the aorta 354. In some cases, the expandable introducer may be introduced into the ascending aorta 355.

FIGS. 22A-D illustrate the sequential movement of a transcatheter aortic valve 356 through introducer sheath assembly 300 over guidewire 350. In the embodiment shown in FIG. 22A the transcatheter aortic valve 356 has a diameter d1 which is larger than the unexpanded diameter d2 of the proximal portion 303 of the expandable introducer sheath which has been deployed in femoral artery 357. After valve 356 passes through hub 302 as shown in FIG. 22B, it causes proximal expandable sheath 303 to expand to an outer diameter d3. This proximal portion 303 may be designed to collapse after the device 356 passes through it. In a different embodiment shown in FIG. 22C the proximal relatively rigid section 303 of introducer sheath 301 has a diameter large enough to permit passage of transaortic valve 356 which does not cause expansion of the sheath until it reaches flexible distal portion 304. At this point, the progress of the valve 356 shown in the embodiments of FIG. 22A and FIG. 22C causes the distal flexible mesh section 304 to expand locally as valve 356 passes through the sheath until it reaches its delivery location. FIG. 22D shows transaortic valve 356 at a location distal from that shown in FIG. 22C. FIGS. 22C and 22D also show the mesh 304 collapsing to a smaller diameter after valve 356 passes through it. Alternatively, if mesh 304 has a diameter in its relaxed state which is the same or larger than its diameter in the expanded state, it will not collapse after a device passes through it.

As shown in FIGS. 23-27B, the proximal semi-rigid section 303 can have a limited expansion capability. This expansion capability may be provided by providing proximal section 303 with a fold or plication 358 such as that shown in the unexpanded state in FIG. 24A where proximal section 303 has a diameter of d2 and FIG. 24B where proximal section 303 has an expanded diameter d3. Similarly, in FIGS. 25A-26 the proximal section 303 can comprise a helically wound coil 359 which may be covered with an expandable membrane (not shown) or a seal 360 may be provided as shown in FIG. 26. Alternatively, as shown in FIGS. 27A and 27B, the proximal section 303 may comprise an external cover such as a membrane combined with expandable reinforcing rings 361 which will expand when placed under pressure by a device such as a heart valve passing through proximal section 303. The foregoing examples are not exhaustive.

Proximal semi-rigid section 303 can be fabricated in a variety of additional ways in which an expandable polymer tube can be reinforced with a metal or other material which either has no expansion capability or a limited expansion capability. Limited expansion capability can be imparted by coiled or braided structures which are embedded in a polymer tube such as those disclosed in U.S. Pat. Nos. 5,527,282; 4,655,771; 4,954,126; 5,061,275 and 5,221,261, the disclosures of which are incorporated by reference herein. A wide variety of polymers and metals may be used for these purposes, provided that the resulting structure will substantially resist collapse. When so constructed, the proximal portion will provide more effective hemostasis at the access point such as femoral artery access point 351 and the vessel puncture site 352 as shown in FIG. 21, where the sheath intersects with and penetrates through tissue and the wall of a blood vessel.

FIGS. 28-30B illustrate in more detail examples of distal flex section 304 which may be used in the present invention. FIG. 28 shows distal flex section having a sealed mesh end 362. FIGS. 29A and 29B illustrate a distal flex section 304 provided with an anti-inversion seam 363. FIGS. 30A and 30B illustrate a distal flex section 304 provided with an anti-inversion spine 364. The anti-inversion elements provide extra support so that the mesh does not fold when devices are moved through the lumen of mesh 304.

Figure 31A:
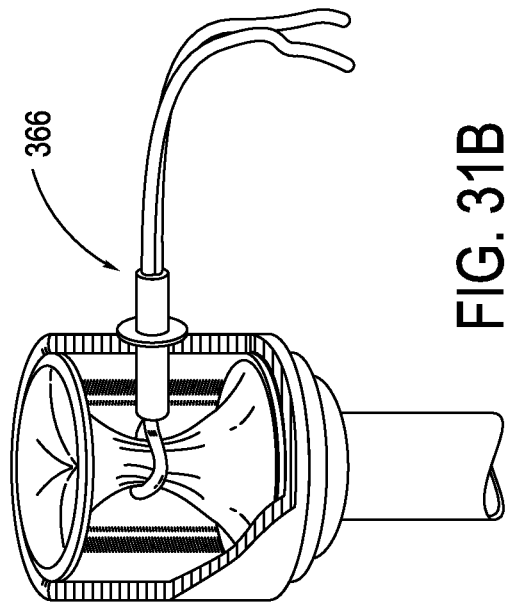
FIGS. 31A, 31B, 31C and 31D illustrate various hemostatic valve constructions which may be used with the sheath assembly.
Figure 31B:
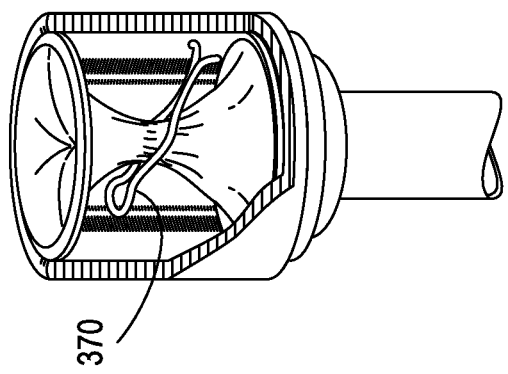
Figure 31C:
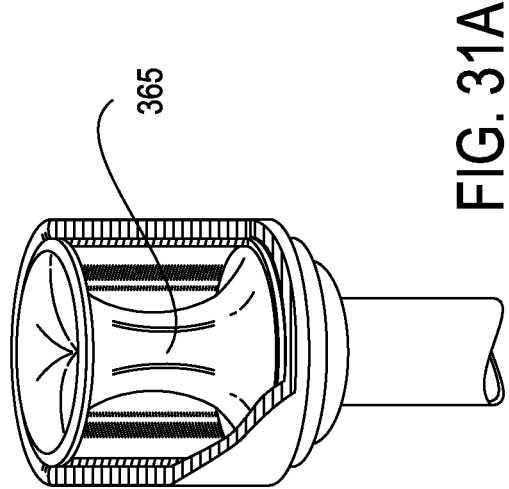
Figure 31D:
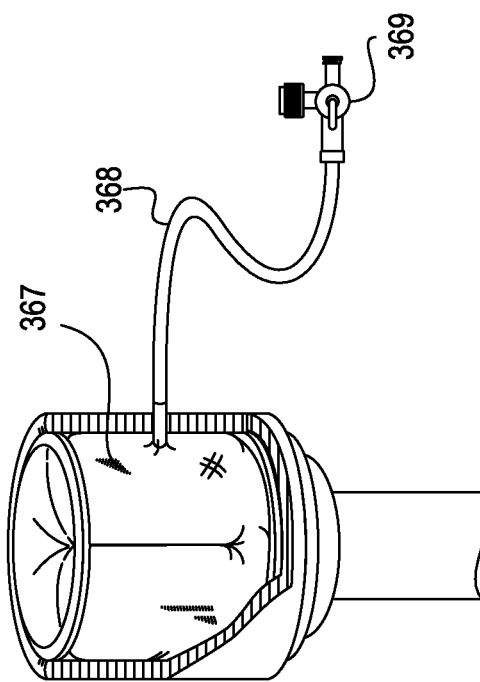

FIGS. 31A-31D show various types of hemostasis valves 324 which may be used in conjunction proximal hub 302 as more generally indicated in FIG. 17. More specifically, FIG. 31A illustrates a valve comprising a necked down portion 365. FIG. 31B shows a valve combined with a rummel 366 which can be used to control its diameter. FIG. 361C illustrates a fluid filled toroidal balloon sphincter 367 which is provided with a fill tube 368 and a shut off valve 369. FIG. 31D illustrates a valve assembly in which a wire spring clip 370 is used to control the diameter of the valve.

In use, the embodiment of the present invention illustrated in FIGS. 13-31D proceeds through the steps of assembling the dilator assembly 305 and the sheath assembly 301 by entrapping the distal region of mesh 304 between dilator tip 308 and the distal portion of dilator sheath 307 as shown, for example, in FIGS. 16D-16F. Clip 309 is then used to place mesh 304 under tension as shown in FIGS. 20A and 20B. This causes mesh 304 to assume a collapsed configuration by reason of the tension placed upon it. This combined assembly of sheath 301 and dilator assembly 305 is then introduced into the vascular system as shown in FIG. 21 as described above. When the distal region of the sheath is at its desired location in the vasculature, the clip is removed and the dilator sheath is disengaged from the dilator tip by advancing the dilator tip away from the distal region of the dilator sheath by moving dilator shaft 306 distally. This frees the distal portion of mesh 304 which allows it to expand which, in turn, permits removal of dilator assembly 305 from the sheath assembly 301. A medical device such as a transcatheter aortic valve 356 can then be advanced through the proximal region 303 and the distal region 304 of the sheath assembly as shown in FIGS. 22A-22D. Once the medical device has been deployed, the sheath assembly 301 can be removed from the patient along with guidewire 350 to complete the device deployment procedure.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. An expandable sheath assembly for deploying a device to a distal location in a blood vessel comprising:
   an introducer sheath comprising a relatively flexible distal portion and a relatively stiff proximal portion, the distal portion comprising a mesh, the introducer sheath having a lumen extending therethrough;
   a hub affixed to the proximal portion of the introducer sheath;
   a dilator assembly comprising:
      a dilator shaft;
      a dilator tip affixed to a distal end of the dilator shaft, a proximal region of the dilator tip having a cavity having an internal beveled wall;
      a luer lock affixed to a proximal end of the dilator shaft; and
      a dilator sheath having a lumen through which the dilator shaft extends, a distal region of the dilator sheath having an external beveled wall that is complementary to the internal beveled wall; and
   a clip comprising:
      a hub engaging portion engaged with the hub;
      a sheath tensioning section comprising:
         a luer lock restraint having the luer lock engaged with a proximal side thereof; and
         a dilator sheath restraint having a proximal end of the dilator sheath engaged with a distal side thereof, wherein the sheath tensioning section maintains a relationship between the internal beveled wall and the external beveled wall after relative movement between the dilator sheath and the dilator tip causes gripping of a distal region of the distal portion of the introducer sheath between the internal beveled wall and the external beveled wall, and wherein the hub engaging portion maintains a relationship between the introducer sheath and the dilator assembly after relative movement between the introducer sheath and the dilator assembly places the introducer sheath into tension.

2. The assembly of claim 1 wherein said dilator shaft has a lumen which extends therethrough, said dilator tip having a lumen which extends therethrough and which communicates with the lumen in the dilator shaft, said dilator assembly being configured to be removable from the blood vessel prior to deploying the device in the blood vessel,
   said distal region of said distal portion of said introducer sheath extending over said external beveled wall of said dilator sheath and within said internal beveled wall of said dilator tip such that said distal region of said distal portion of said introducer sheath is gripped in an entrapment region between said beveled walls, said distal region of said distal portion of said introducer sheath directly contacting said external beveled wall and said internal beveled wall, said distal region of said distal portion of said introducer sheath being pulled by the dilator assembly to place said introducer sheath into tension,
   said dilator sheath being axially slidable along said dilator shaft.

3. The assembly of claim 2 wherein said proximal portion of said introducer sheath comprises a reinforcing element which increases the rigidity of said proximal portion.

4. The assembly of claim 2 wherein said proximal portion of said introducer sheath is fabricated from a material which is more rigid than said distal portion.

5. The assembly of claim 2 wherein a distal portion of said mesh is in a free state when said dilator sheath is displaced proximally from said dilator tip and in an entrapped state when said dilator sheath is advanced sufficiently distally into the proximal region of said dilator tip having said internal beveled wall to create said entrapment region.

6. The assembly of claim 2 wherein the distal portion of said introducer sheath is expandable.

7. The assembly of claim 2 wherein the proximal portion of said introducer sheath is expandable.

8. The assembly of claim 2 wherein both the proximal and distal portions of said introducer sheath are expandable.

9. The assembly of claim 2 wherein a proximal end of said introducer sheath is coupled to said hub.

10. The assembly of claim 9 wherein said dilator shaft is slidable within said hub.

11. The assembly of claim 9 wherein said dilator shaft and said dilator sheath are slidable within said hub and said clip is removably coupled to the hub.

12. The assembly of claim 9 wherein said mesh is maintained under tension by said clip.

13. The assembly of claim 11 wherein said clip comprises a housing having a compartment through which said dilator sheath and shaft extend.

14. The assembly of claim 13 wherein said housing comprises said luer lock restraint distal to said luer lock.

15. The assembly of claim 14 wherein said luer lock restraint prevents distal displacement of said dilator shaft when said luer lock abuts said restraint.

16. The assembly of claim 15 wherein said compartment comprises said dilator sheath restraint distal to said luer lock restraint and which abuts said proximal end of said dilator sheath.

17. The assembly of claim 16 wherein said dilator sheath restraint limits the range of axial displacement of said dilator sheath.

18. The assembly of claim 11 wherein said clip is provided with a handle on its external wall.

19. The assembly of claim 9 wherein said hub is provided with a hemostasis valve.

* * * * *